(12) United States Patent
Hirata

(10) Patent No.: US 6,951,537 B2
(45) Date of Patent: Oct. 4, 2005

(54) ENDOSCOPE OF WHICH THE BENDING PART IS OPERATED BY FLUID SUPPLY OR EXHAUSTION

(75) Inventor: Yasuo Hirata, Hachioji (JP)

(73) Assignee: Olympus Corporation (JP)

( * ) Notice: Subject to any disclaimer, the term of this patent is extended or adjusted under 35 U.S.C. 154(b) by 20 days.

(21) Appl. No.: 10/746,492

(22) Filed: Dec. 23, 2003

(65) Prior Publication Data

US 2005/0004433 A1 Jan. 6, 2005

(30) Foreign Application Priority Data

Dec. 24, 2002 (JP) ........................................ 2002-373149
Jun. 23, 2003 (JP) ........................................ 2003-178651

(51) Int. Cl.[7] ................................................. A61B 1/00
(52) U.S. Cl. ........................ 600/152; 600/139; 600/146
(58) Field of Search ................................. 600/139, 146, 600/152; 138/118, 26

(56) References Cited

U.S. PATENT DOCUMENTS 4,976,191 A 12/1990 Suzumori et al.
5,577,992 A 11/1996 Chiba et al.

FOREIGN PATENT DOCUMENTS

JP 11-318817 11/1999
JP 2001-258819 9/2001

*Primary Examiner*—Beverly M. Flanagan
*Assistant Examiner*—Matthew Kasztejna
(74) *Attorney, Agent, or Firm*—Ostrolenk, Faber, Gerb & Soffen, LLP

(57) ABSTRACT

An endoscope whose bending section is moved with supply or discharge of fluid comprises: a fluid-pressure actuator that is included as a bending section in an insertion unit and has fluid chambers associated with a plurality of bending directions; and fluid supply tubes over which fluid is supplied from a fluid pressure source to the respective fluid chambers of the fluid-pressure actuator or fluid supplied to the respective fluid chambers is discharged. The fluid-pressure actuator comprises: a soft multi-lumen tube that has a center through hole and a plurality of penetrating holes which surrounds the center through hole and which realizes the fluid chambers; an internal tubular member that is inserted in the center through hole; and an external tubular member that is put on the periphery of the multi-lumen tube with a gap, which allows each fluid chamber to axially stretch and radially slightly expand during supply of fluid to the fluid chamber and thus eases bending, created between them.

23 Claims, 34 Drawing Sheets

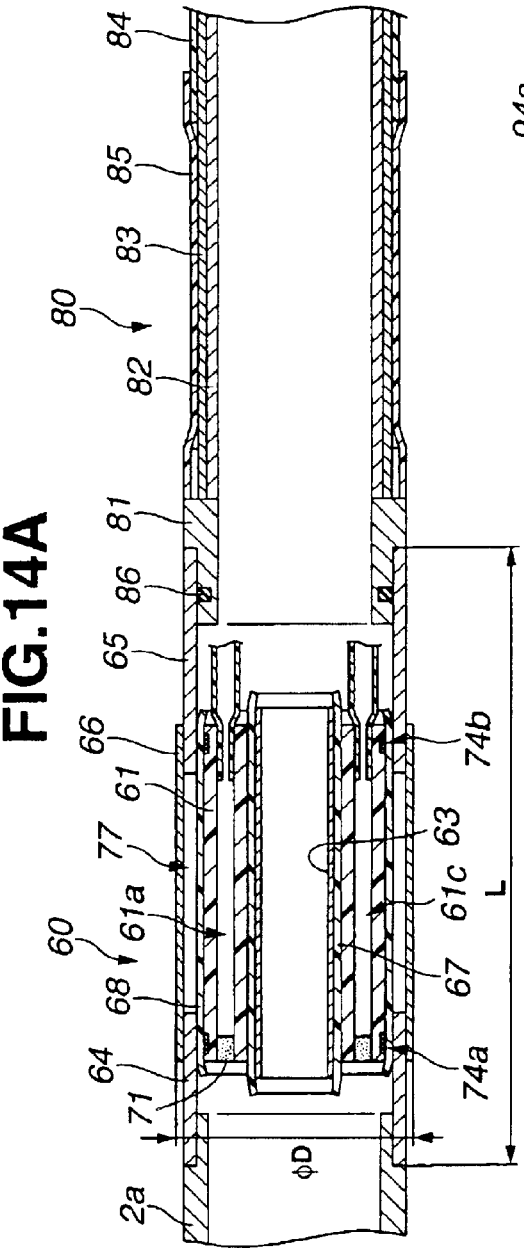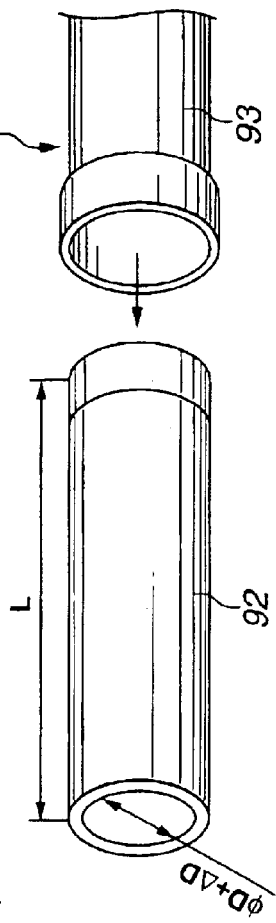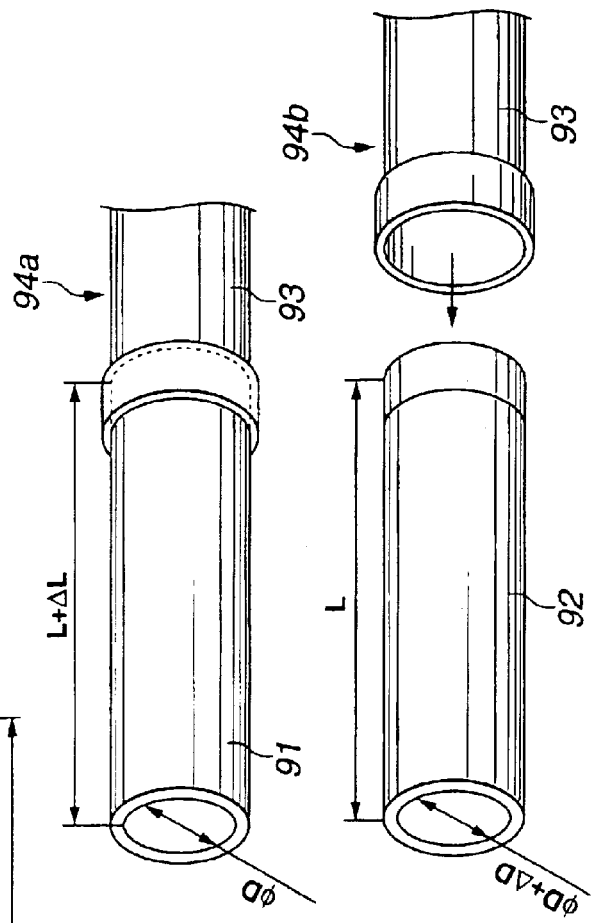
FIG.14A
FIG.14B
FIG.14C

FIG.17A
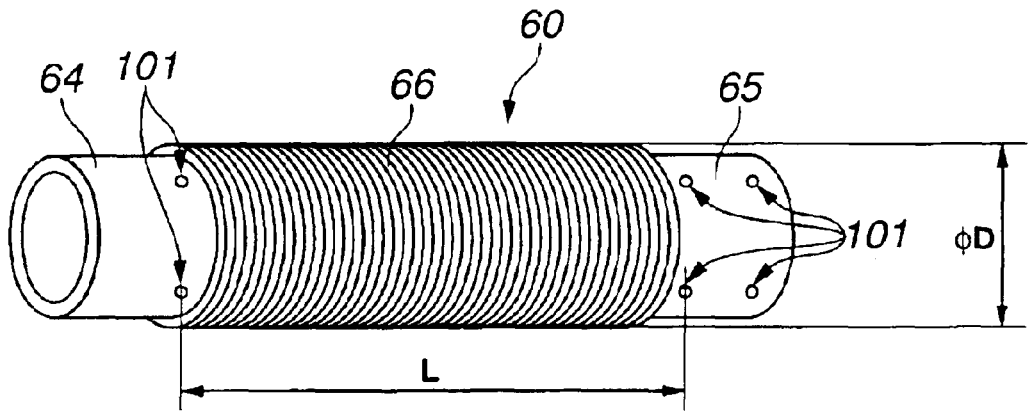
FIG.17B
FIG.17D
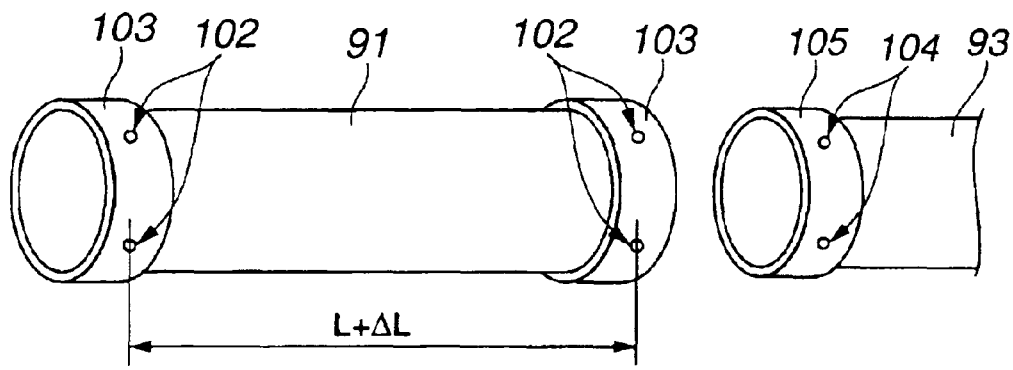
FIG.17C
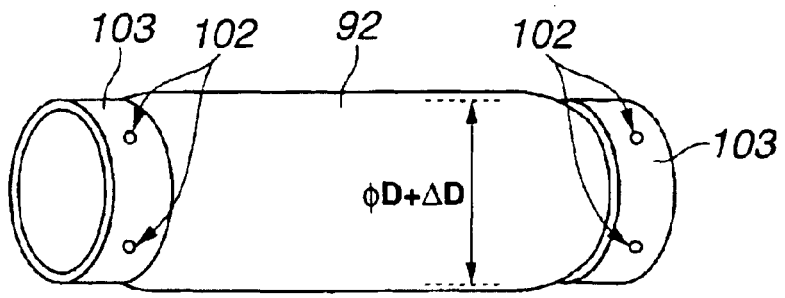

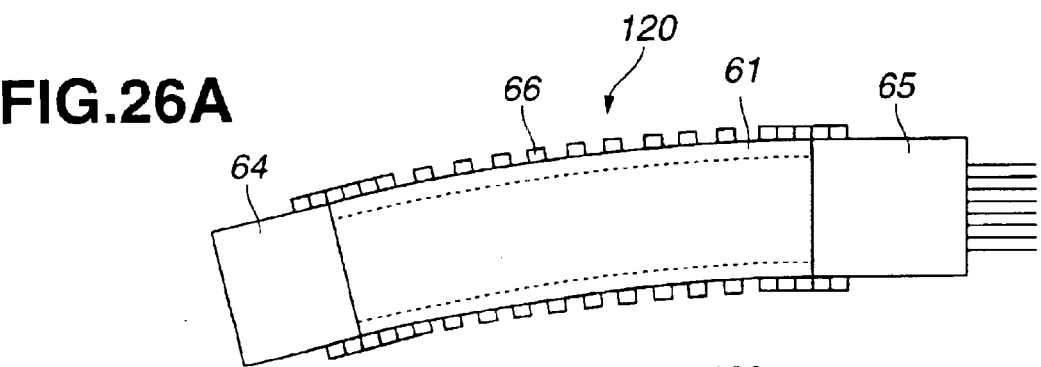
FIG.26A
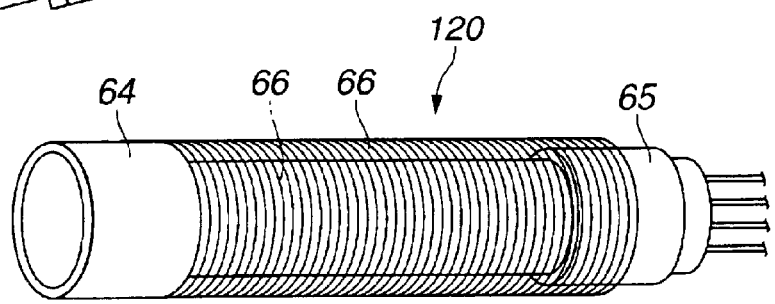
FIG.26B
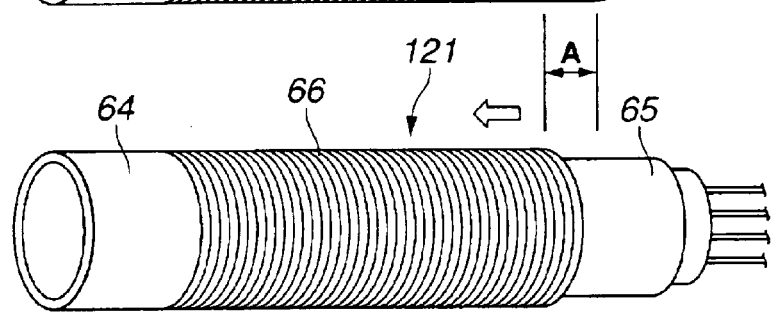
FIG.26C
FIG.26D
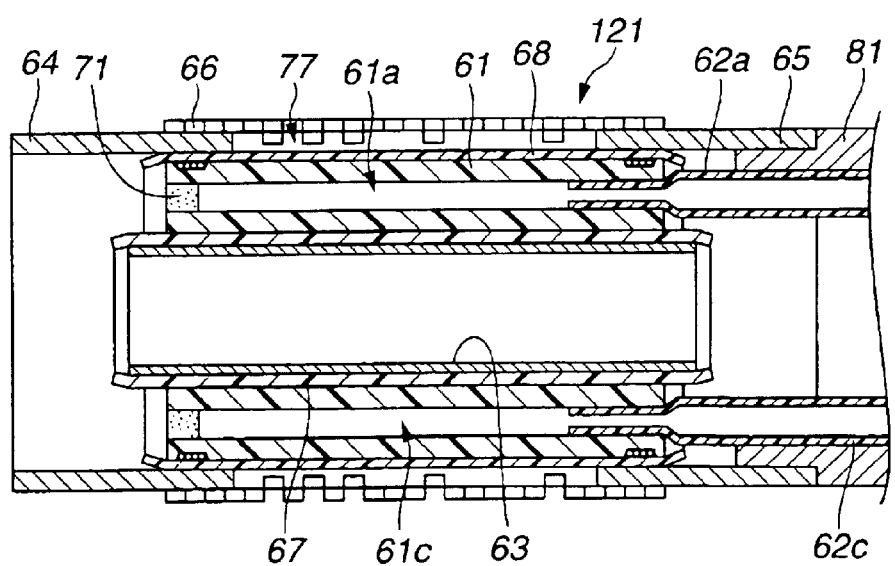

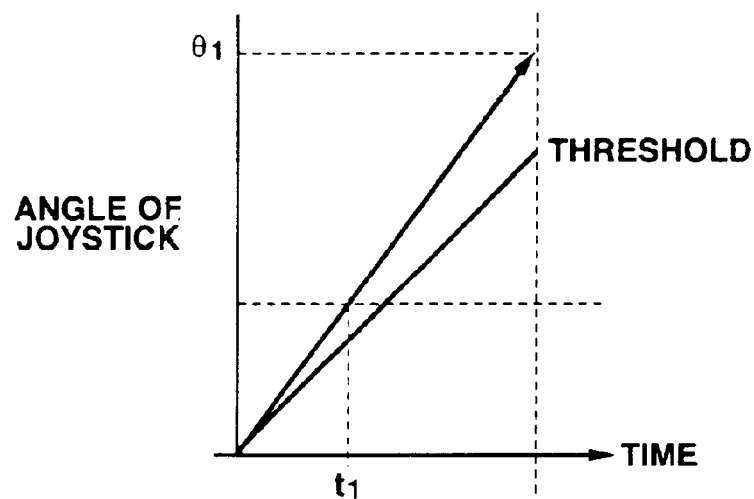
FIG.29A ANGLE OF JOYSTICK
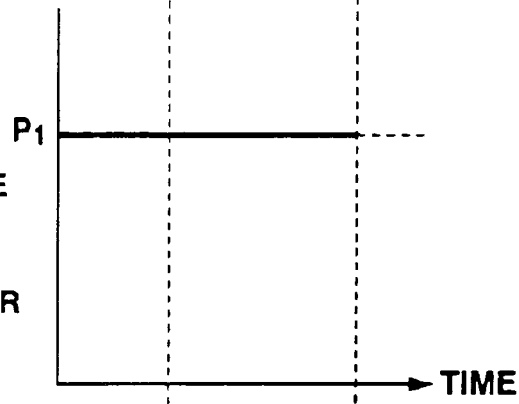
FIG.29B PRESSURE OF FLUID SUPPLIED FROM REGULATOR
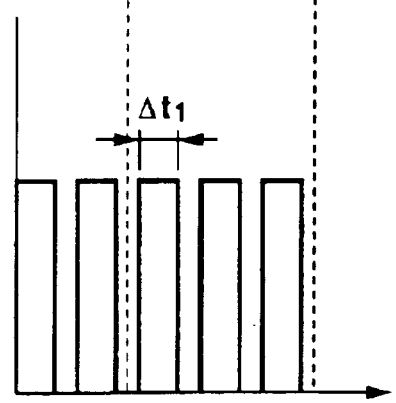
FIG.29C VALVE UNIT

FIG. 30A ANGLE OF JOYSTICK
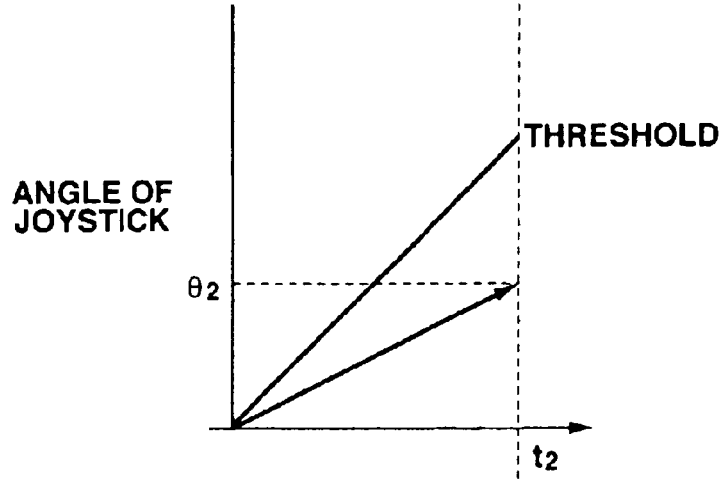
FIG. 30B PRESSURE OF FLUID SUPPLIED FROM REGULATOR
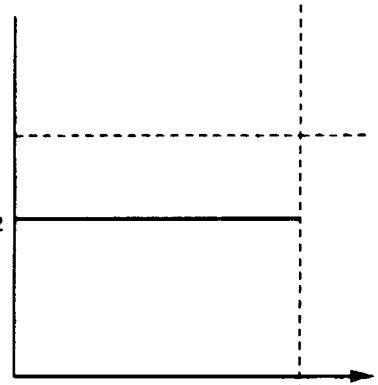
FIG. 30C VALVE UNIT
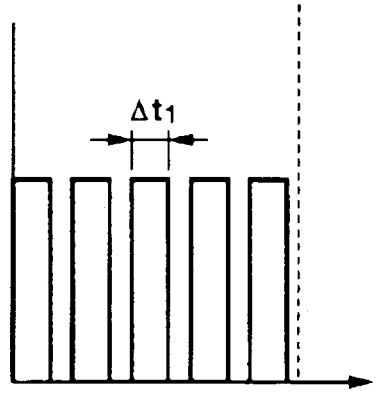

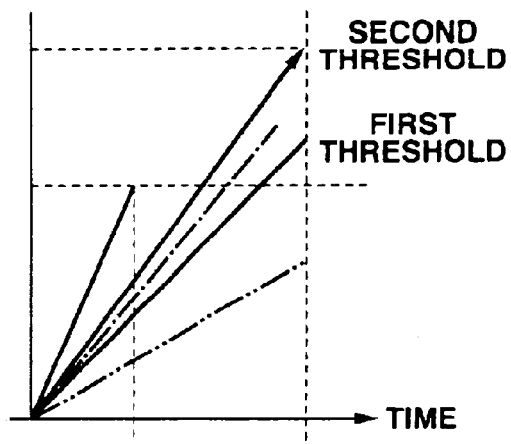
FIG.31A  ANGLE OF JOYSTICK
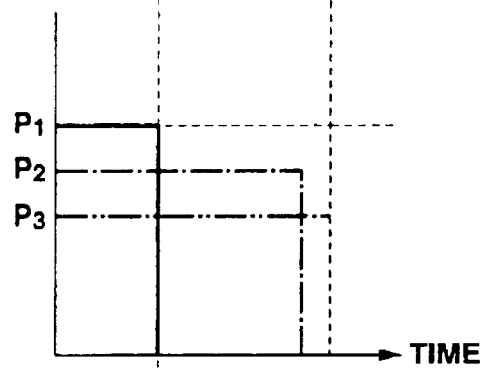
FIG.31B  PRESSURE OF FLUID SUPPLIED FROM REGULATOR
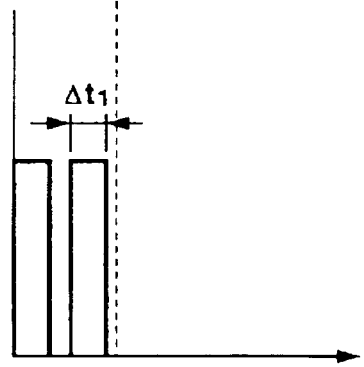
FIG.31C  VALVE UNIT

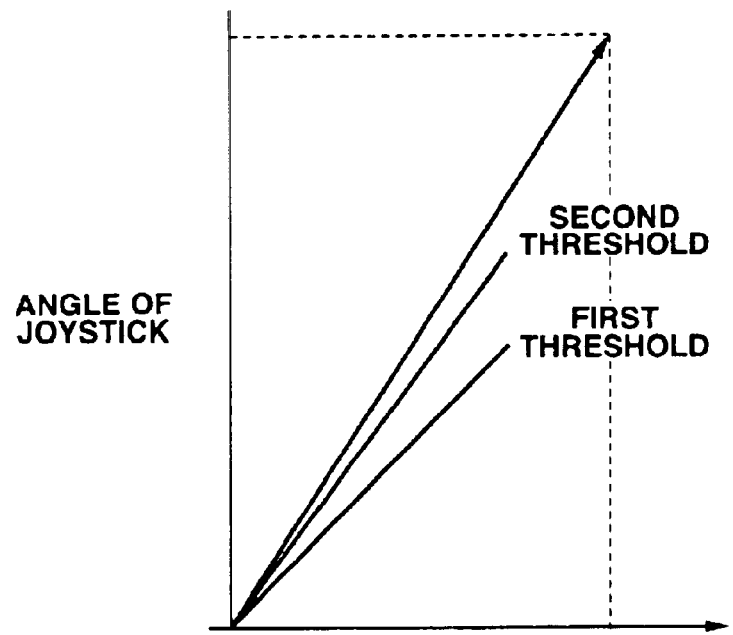
FIG.32A ANGLE OF JOYSTICK
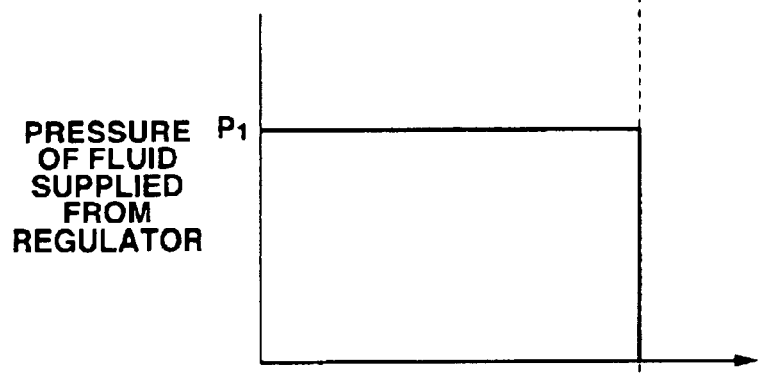
FIG.32B PRESSURE OF FLUID SUPPLIED FROM REGULATOR
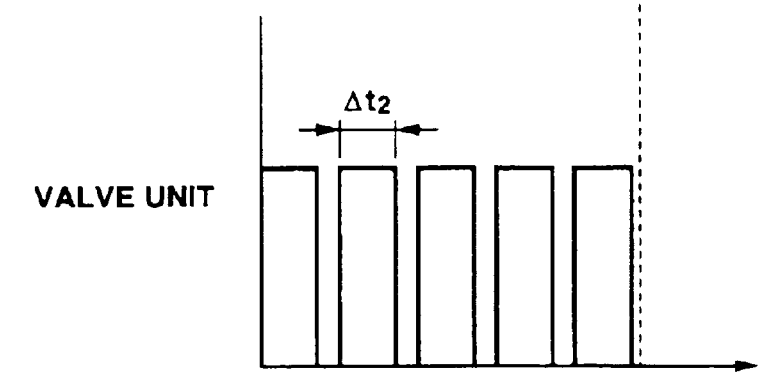
FIG.32C VALVE UNIT

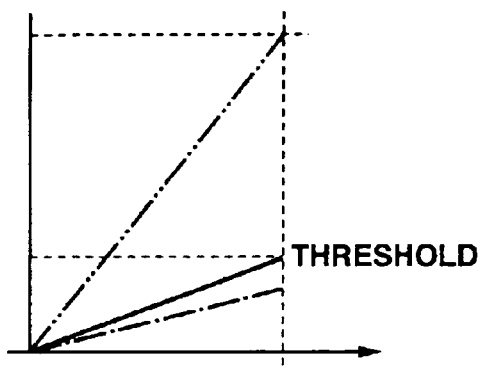
FIG.33A  ANGLE OF JOYSTICK / THRESHOLD
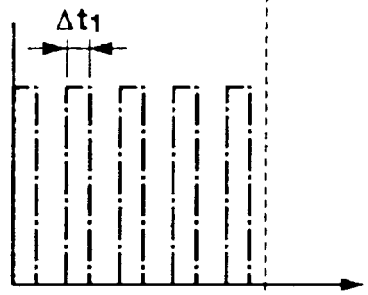
FIG.33B  VALVE UNIT
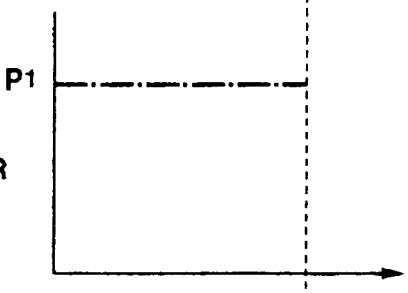
FIG.33C  REGULATOR
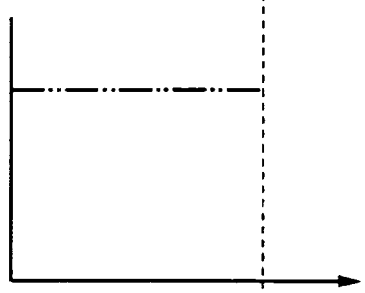
FIG.33D  VALVE UNIT
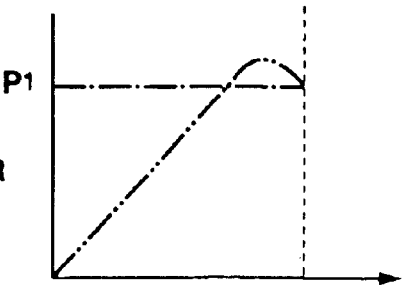
FIG.33E  REGULATOR

ENDOSCOPE OF WHICH THE BENDING PART IS OPERATED BY FLUID SUPPLY OR EXHAUSTION

This application claims the benefit of Japanese Application No. 2003-178651 filed on Jun. 23, 2003, No. 2002-373149 filed on Dec. 24, 2002, No. 2001-370398 filed on Dec. 4, 2001, the contents of which are incorporated by reference.

BACKGROUND OF THE INVENTION

1. Field of the Invention

The present invention relates to an endoscope that has a bending section formed with a fluid-pressure actuator as the distal part of an elongated insertion unit which is inserted into a lumen, and that is adapted to industrial or medical use.

2. Description of the Related Art

In general, endoscopes adaptable to industrial or medical use have an insertion unit that is inserted into a lumen. A type of endoscope having a soft and elongated insertion unit has a bending section formed as the distal part of the insertion unit. When the bending section is bent, for example, an observing direction can be set to any direction.

As far as endoscopes for industrial use are concerned, the insertion unit is requested to be inserted 30 m or more. In this case, if a bending mechanism is of a type having angling wires that are pulled in order to move the bending section of an endoscope, a user may find it hard to bend the bending section as he/she intends to. This is because sliding resistance or the like occurs between the angling wires and other members. A proposal has been made of an endoscope having a fluid-pressure actuator, which bends with supply of fluid such as air, as the bending mechanism for a bending section.

For example, U.S. Pat. No. 5,577,992 has disclosed a bending section of an endoscope that is finely thin and can be bent at a large bending angle while exhibiting a small radius of curvature at a certain point. The bending section of the endoscope has a member, which restricts expansion of a stretchable and contractile member, wound about the stretchable and contractile member, whereby expansion of the stretchable and contractile member in a radial direction is restricted. Consequently, a pressurized pressure chamber (fluid chamber in the present embodiment) stretches largely forwards and eventually bends largely.

SUMMARY OF THE INVENTION

An endoscope in accordance with the present invention whose bending section is moved with supply or discharge of fluid comprises: a fluid-pressure actuator that is included as a bending section in an insertion unit and has fluid chambers associated with a plurality of bending directions; and fluid supply tubes over which fluid is supplied from a fluid-pressure source to the respective fluid chambers included in the fluid-pressure actuator or fluid supplied to the respective fluid chambers is discharged. The fluid-pressure actuator comprises: a soft multi-lumen tube that has a center through hole and a plurality of penetrating holes which serves as the fluid chambers and surrounds the central hole; an internal tubular member inserted in the center through hole; and an external tubular member placed on the periphery of the multi-lumen tube with a gap, which allows each fluid chamber to axially stretch and slightly radially expand and thus eases bending, created between them. Consequently, the bending motion of the fluid-pressure actuator becomes smooth and the durability thereof improves.

The above and other objects of the invention, and the features and advantages thereof will be more clearly understood from the following description with reference to the accompanying drawings.

BRIEF DESCRIPTION OF THE DRAWINGS

FIG. 14A is a sectional view showing the fluid-pressure actuator and flexible tube formation member that are integrated with each other;

FIG. 14B is an explanatory diagram showing a first bending cover and a flexible tube cover integrated with the first bending cover;

FIG. 14C is an explanatory diagram showing a second bending cover and the flexible tube cover;

FIG. 17A is an explanatory diagram showing a cover attachment structure of the fluid-pressure actuator;

FIG. 17B is an explanatory diagram showing an attachment structure for use in attaching the first bending cover to the fluid-pressure actuator;

FIG. 17C is an explanatory diagram showing an attachment structure for use in attaching the second bending cover to the fluid-pressure actuator;

FIG. 17D is an explanatory diagram showing an attachment structure for use in attaching the flexible tube cover to the fluid-pressure actuator;

FIG. 17 is an explanatory diagram showing the attachment structures for use in attaching the bending covers and flexible tube cover to the fluid-pressure actuator;

FIG. 26A is an explanatory diagram showing the structure of a conventional fluid-pressure actuator;

FIG. 26B shows an external coil extended to bases using the overall length naturally;

FIG. 26C shows a fluid-pressure actuator having a compressed external coil extended to bases;

FIG. 26D is an explanatory sectional view showing the structure of the fluid-pressure actuator;

FIG. 29A is an explanatory diagram graphically showing the relationship between an angle at which a joystick is tilted and a time required to tilt the joystick at the angle which exceeds a threshold;

FIG. 29B indicates a pressure value of the regulator attained when the relationship exceeds the threshold;

FIG. 29C indicates the supply of fluid from a valve unit achieved when the relationship exceeds the threshold;

FIG. 30A is an explanatory diagram graphically showing the relationship between an angle at which the joystick is tilted and a time required to tilt the joystick at the angle which is equal to or smaller than the threshold;

FIG. 30B indicates a pressure value of the regulator attained when the relationship is equal to or smaller than the threshold;

FIG. 30C shows the supply of fluid from the valve unit achieved when the relationship is equal to or smaller than the threshold;

FIG. 31A graphically shows a tilting speed at which the joystick is tilted at an angle in relation with two thresholds;

FIG. 31B indicates the pressure value of the electropneumatic regulator drawn out from the tilting speed at which the joystick is tilted at an angle, and the two thresholds;

FIG. 31C indicates supply of fluid from a valve unit;

FIG. 32A indicates that the angle at which the joystick is tilted is large and that the tilting speed exceeds the second threshold;

FIG. 32B indicates the pressure value of the regulator;

FIG. 32C indicates the supply of fluid from the valve unit;

FIG. 33A is an explanatory diagram concerning a state in which the speed at which the joystick is tilted is equal to or smaller than a threshold and a state in which the speed is equal to or larger than the threshold;

FIG. 33B indicates the supply of fluid from the valve unit achieved when the speed at which the joystick is tilted is equal to or smaller than the threshold;

FIG. 33C indicates the pressure value of the regulator attained when the speed at which the joystick is tilted is equal to or smaller than the threshold;

FIG. 33D indicates the supply of fluid from the valve unit achieved when the speed at which the joystick is tilted is equal to or larger than the threshold;

FIG. 33E indicates the pressure value of the regulator attained when the speed at which the joystick is tilted is equal to or larger than the threshold;

DETAILED DESCRIPTION OF PREFERRED EMBODIMENTS

Figure 1:
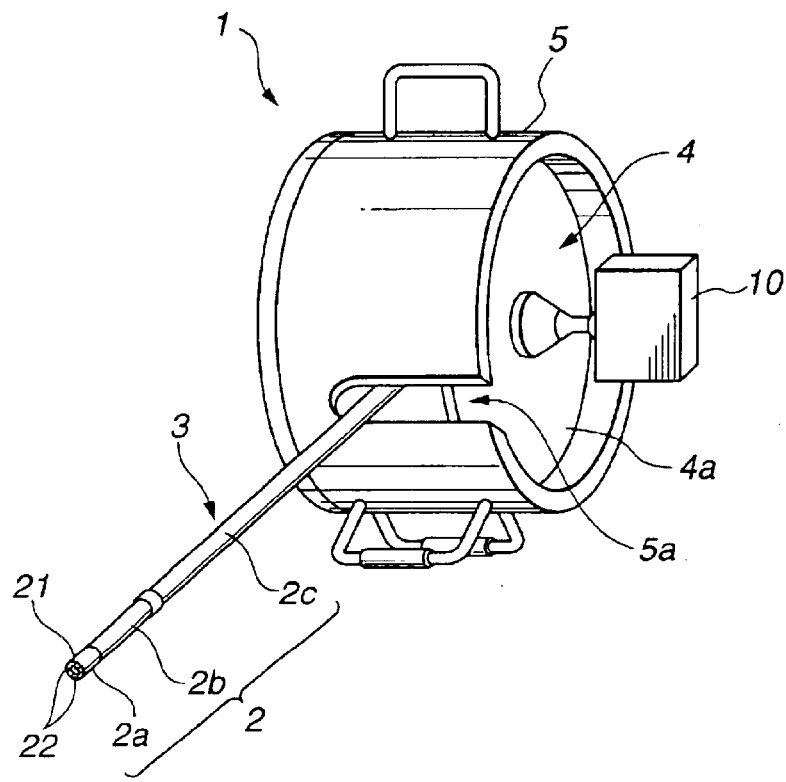
FIG. 1 is an explanatory diagram showing the structure of an endoscopic apparatus.

Referring to the drawings, an embodiment of the present invention will be described below.

As shown in FIG. 1, an endoscopic apparatus 1 in accordance with the present embodiment mainly comprises an endoscope 3 having an elongated insertion unit 2, a drum 4 about which the insertion unit 2 is wound, and a drum container 5 in which the drum 4 is stored. Reference numeral 10 denotes, for example, an LCD monitor mounted on an upper flange 4a of the drum 4. An endoscopic image formed by the endoscope 3 is displayed on the LCD monitor 10.

The insertion unit 2 of the endoscope 3 is ejected to outside from a notch 5a formed in the drum container 5. The insertion unit 2 has a distal rigid section 2a, a bending section 2b, and a flexible tube 2c concatenated in that order from the distal end thereof. The bending section 2b includes a fluid-pressure actuator that will be described later and that bends the bending section 2b in a desired direction with supply of fluid to a desired fluid chamber. The flexible tube 2c is formed with a soft elongated flexible member that adjoins the bending section 2b.

The distal rigid section 2a has an observation window 21 formed in, for example, the center of a distal end thereof. A plurality of LED lights 22 is arranged around the observation window 21. An observing means, for example, a CCD (not shown) is incorporated in the distal rigid section 2a.

The distal rigid section 2a and bending section 2b of the insertion unit 2 are freely attachable or detachable to each other, and the bending section 2b and flexible tube 2c thereof are freely attachable or detachable to each other. Moreover, the observing means is not limited to the CCD but may be a C-MOS or an image guide fiber. Furthermore, the illumination optical system is not limited to the LED lights but may be a light guide fiber or the like.

Figure 2A:
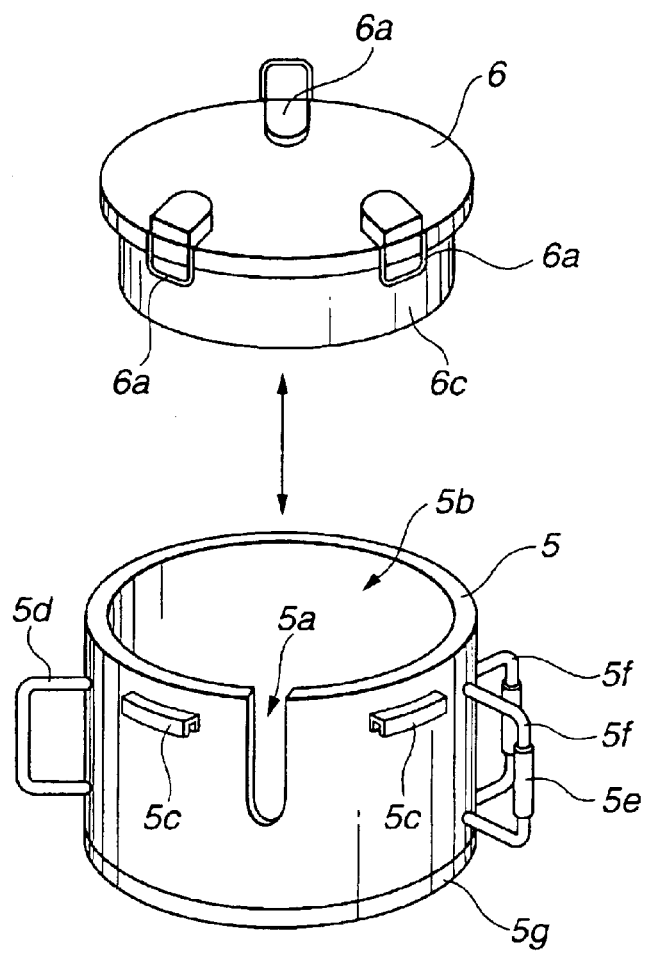
FIG. 2A is an explanatory diagram showing a drum container and a housing.
Figure 2B:
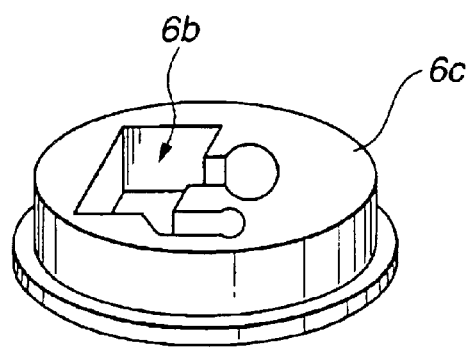
FIG. 2B is an explanatory diagram showing a cushion member for the housing.

As shown in FIG. 2A, a lid 6 for blocking a storage opening 5b is mounted on the drum container 5. The lid 6 has cramps 6a. The cramps 6a are hooked on holding metals 5c fixed to the drum container 5.

A grip 5d and legs 5f having anti-slip rubbers 5e are fixed to the periphery of the drum container 5, and an anti-slip rubber 5g is fixed to the margin of the bottom.

As shown in FIG. 2A, a cushion member 6c having a recess 6b in which the LCD monitor 10 is fitted is attached to the lid 6.

Figure 3:
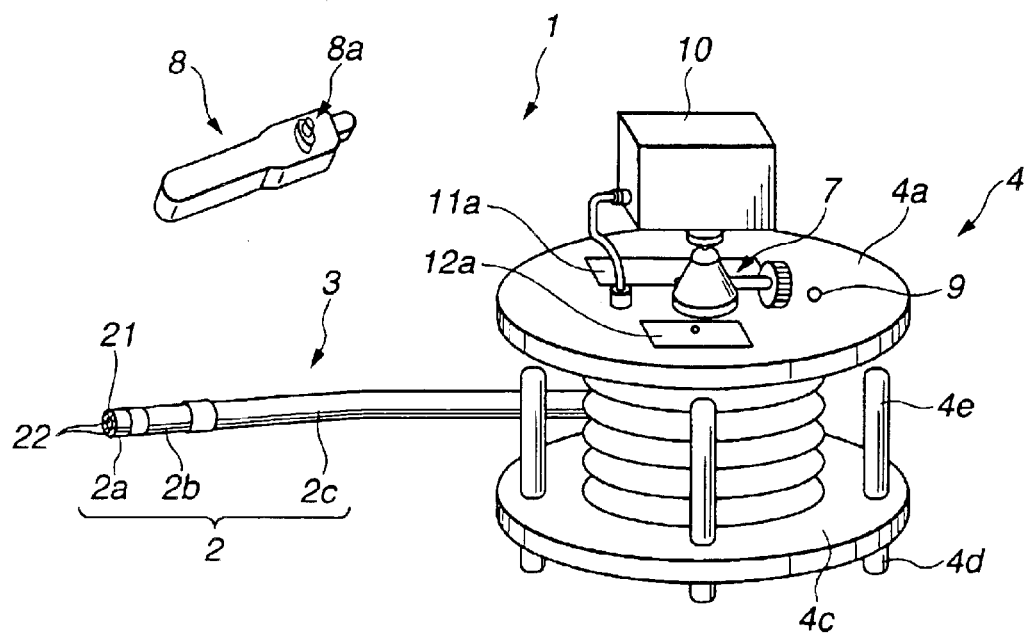
FIG. 3 is an explanatory diagram showing a drum and an endoscope whose insertion unit is wound about the drum.

As shown in FIG. 3, the drum 4 taken out of the drum container 5 is shaped like a bobbin. The drum 4 comprises a disk-like upper flange 4a, a tubular insertion unit take-up 4b about which the insertion unit 2 is wound, and a disk-like lower flange 4c. Rubber legs 4d are fixed to one side of the lower flange 4c. Reference numeral 11a denotes a support bar.

The LCD monitor 10 is mounted on the upper flange 4a with a monitor locking member 7 between them. Moreover, a battery lid 11a covering a buttery casing and a cylinder lid 12a covering a cylinder casing are freely opened or closed on the upper flange 4a. The upper flange 4a includes a light receiver 9. The light receiver 9 receives, for example, communication light emitted from a remote controller 8. The remote controller 8 has a joystick 8a or the like that is used to bend the bending section 2b of the endoscope 3 or to give instructions.

Figure 4A:
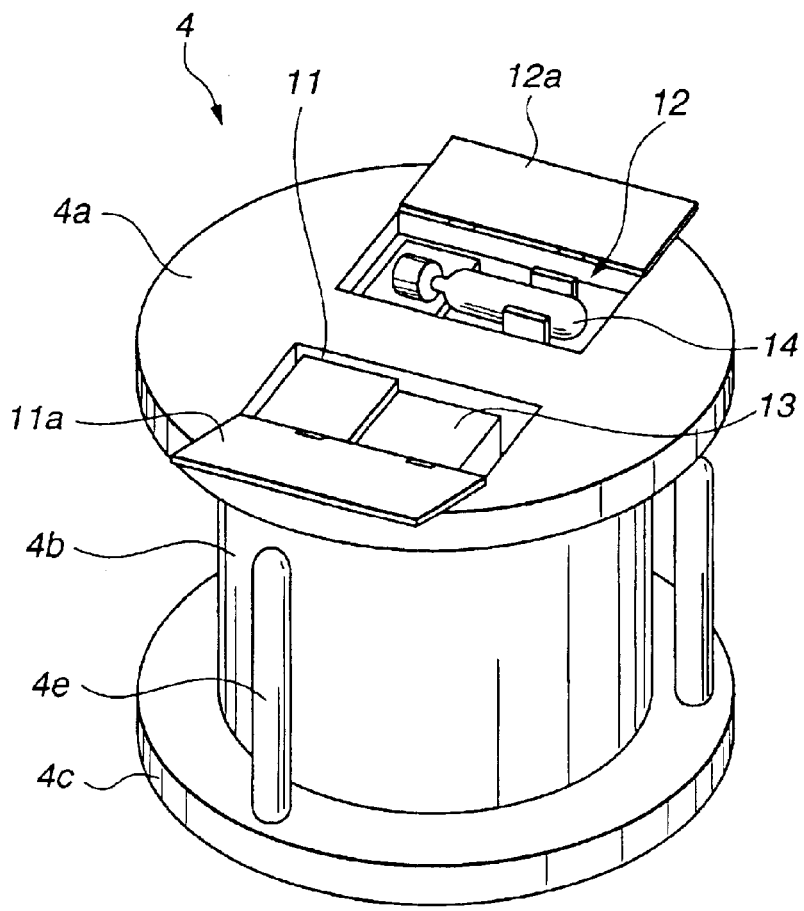
FIG. 4A is an explanatory diagram showing lids and casings formed in an upper flange of the drum.

As shown in FIG. 4A, the battery lid 11a and cylinder lid 12a in the upper flange 4a of the drum 4 can be freely opened or closed. When the battery lid 11a is opened, a battery 13 can be stored in the battery casing 11 or can be replaced with a new one. When the cylinder lid 12a is opened, a gas cylinder 14 serving as a fluid pressure source can be stored in the cylinder casing 12 or can be replaced with a new one.

Figure 4B:
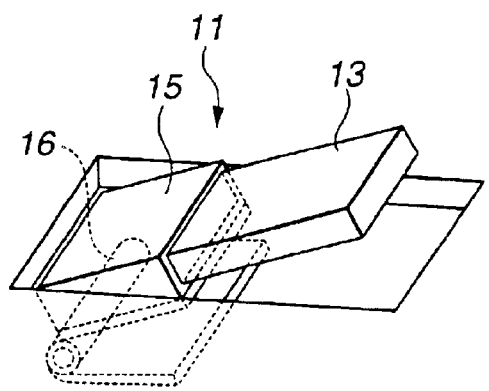
FIG. 4B is an explanatory diagram showing a battery casing.

As shown in FIG. 4B, the battery casing 11 has a battery accommodation socket 15 and a battery hinge 16. The battery accommodation socket 15 is shaped like a box in which the battery 13 is stored. The battery hinge 16 causes the battery accommodation socket 15 to hinge vertically.

Figure 4C:
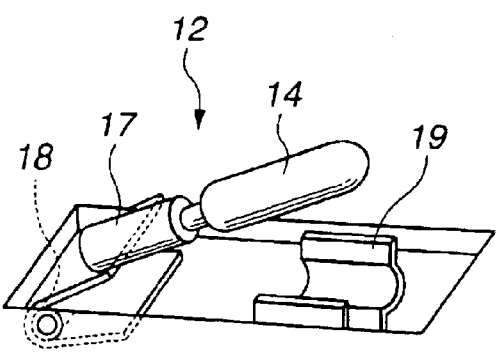
FIG. 4C is an explanatory diagram showing a cylinder casing.

On the other hand, as shown in FIG. 4C, the cylinder casing 12 includes a cylinder coupler 17, a cylinder hinge 18, and a cylinder holder 19. The gas cylinder 14 is coupled to the cylinder coupler 17. The cylinder hinge 18 causes the cylinder coupler 17 to hinge vertically. The cylinder holder 19 holds the gas cylinder 14.

The gas cylinder 14 is filled with an incombustible gas, for example, carbon dioxide, chlorofluorocarbon, nitrogen, helium, argon, or nitrogen. In the present embodiment, a gas cylinder filled with nitrogen is employed.

Figure 5:
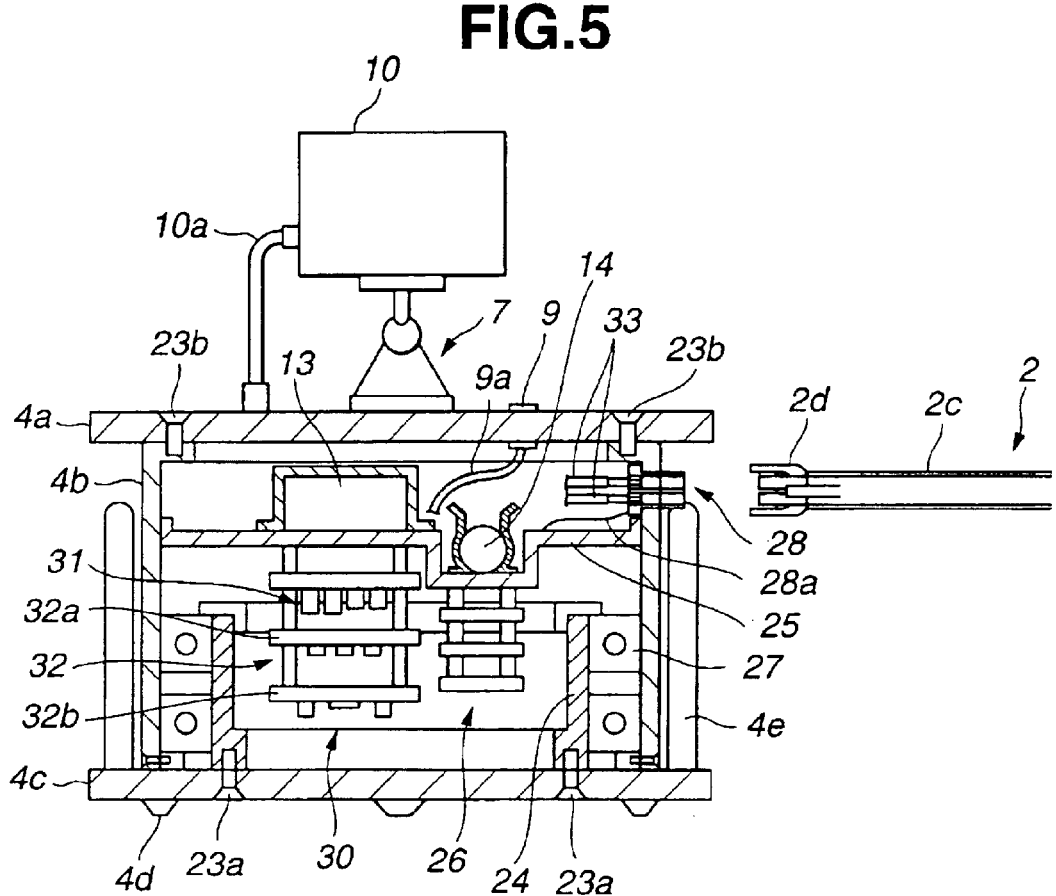
FIG. 5 is an explanatory diagram showing the structure of the drum.

As shown in FIG. 5, the drum 4 comprises a stationary section composed mainly of the lower flange 4c and a rotary section composed of the upper flange 4a and insertion unit take-up 4b. The rotary section rotates relative to the stationary section.

A tubular locking member 24 is fixed as an integral part of the lower flange 4c at a predetermined position using first locking screws 23a.

On the other hand, the upper flange 4a and insertion unit take-up 4b are integrated with each other using second locking screws 23b. A partition 25 that bisects the hollow of the insertion unit take-up 4b is locked in the insertion unit take-up 4b. A bearing member 27 is disposed on the internal surface of the insertion unit take-up 4b below the partition 25. The bearing member 27 slides relative to the locking member 24. Incidentally, a resin ring that can slide readily may be substituted for the bearing member 27.

A drum-side connector 28 is fixed to the periphery of the insertion unit take-up 4b above the partition 25 in the drawing. An endoscope-side connector 2d fixed to the proximal end of the flexible tube 2c is freely detachably attached to the drum-side connector 28.

The battery 13, the gas cylinder 14, a fluid supply level control unit 30, and a CCU 26 are mounted on the partition 25 locked in the insertion unit take-up 4b. The fluid supply level control unit 30 controls the supply of fluid from the gas cylinder 14 to the fluid-pressure actuator. The CCU 26 includes a signal processor that produces a driving signal with which the CCD is driven, or converts an image signal sent from the CCD into a video signal.

The fluid supply level control unit 30 includes a valve unit 31 and a valve controller 32. The valve unit 31 includes an electromagnetic valve unit that has relation to the fluid-pressure actuator. The valve controller 32 comprises a plurality of control circuit boards 32a and 32b for controlling the valve unit 31.

The valve controller 32 and valve unit 31 are electrically connected to each other. Moreover, a video cable 10a extending from the LCD monitor 10 is electrically coupled to the CCU 26. Furthermore, a signal cable 9a extending from the light receiver 9 is electrically coupled to the valve controller 32 included in the fluid supply level control unit 30. A signal line 28a extending from the drum-side connector 28 is electrically coupled to the CCU 26. Moreover, a plurality of fluid supply tubes 33a, 33b, 33c, and 33d extending from the drum-side connector 28 are coupled to the valve unit 31. A regulator that is not shown and that is included in a fluid pressure source for controlling the pressure of the gas cylinder 14, and a tube over which fluid of a predetermined pressure is supplied are located near the gas cylinder 14.

Figure 6A:
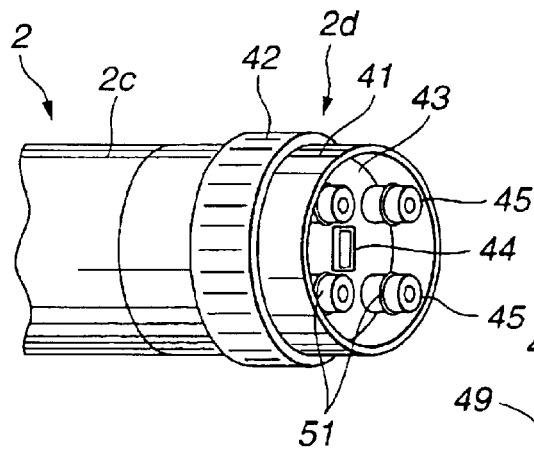
FIG. 6A is an explanatory diagram showing the structure of an endoscope-side connector.

As shown in FIG. 6A, the endoscope-side connector 2d mainly comprises an endoscope-side base 41 and a coupler 42. The coupler 42 can be freely rotated relative to the endoscope-side base 41, and has a female screw threaded on the internal surface thereof.

The endoscope-side base 41 includes a first base body 43. An endoscope-side electric contact 44 that is, for example, a male contact is projecting in the center of the base body 43. An imaging cable that is not shown and that extends from a C-MOS and runs through the insertion unit 2 is coupled to the endoscope-side electric contact 44.

A plurality of fluid coupling members 45 is projecting around the endoscope-side electric contact 44. The fluid coupling members 45 are formed with communication members. The proximal parts of fluid tubes that will be described later and that extend from the fluid-pressure actuator and run through the insertion unit are coupled to the fluid coupling members 45.

Figure 6B:
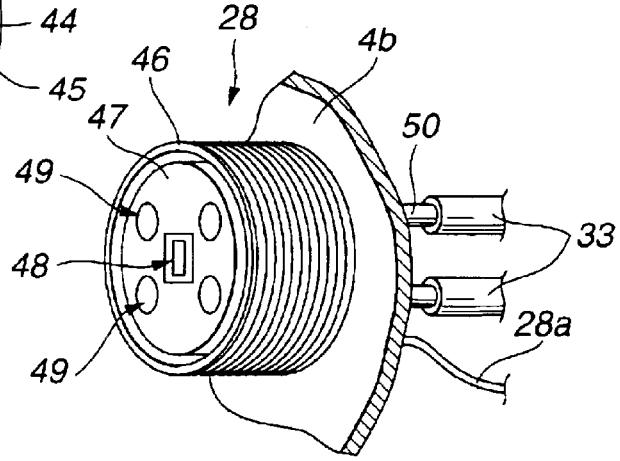
FIG. 6B is an explanatory diagram showing the structure of a drum-side connector.

In contrast, as shown in FIG. 6B, the drum-side connector 28 comprises a drum-side base 46 and a base body 47. The drum-side base 46 has a male screw, which is meshed with the female screw threaded on the coupler 42, threaded thereon. The base body 47 is fitted in the bore of the drum-side base 46. The endoscope-side base 41 is placed in a gap between the base body 47 and drum-side base 46.

A drum-side electric contact 48 that is a female contact is formed in the center of the base body 47. The endoscope-side electric contact 44 is electrically joined to the drum-side contact 48. The signal line 28a is electrically coupled to the drum-side electric contact 48.

A plurality of communication holes 49 is formed around the drum-side electric contact 48. The fluid supply tubes 33a, 33b, 33c, and 33d communicate with the communication holes 49 via, for example, tubular sleeves 50. When the fluid coupling members 45 are inserted into the communication holes 49, the fluid coupling members 45 communicate with the fluid supply tubes 33a, 33b, 33c, and 33d respectively.

An O ring 51 having elasticity is attached to each of the fluid coupling members 45. Therefore, when the fluid coupling members 45 are inserted into the communication holes 49, the O rings 51 on the fluid coupling members 45 come into close contact with the internal surfaces of the communication holes 49. Consequently, the communication holes 49 are kept watertight.

In order to couple the insertion unit 2 to the drum 4, the fluid coupling members 45 are aligned with the communication holes 49, and fitted into the communication holes 49. Consequently, the fluid coupling members 45 are fitted into the communication holes 49, and the endoscope-side electric contact 44 and drum-side electric contact 48 are electrically joined with each other.

Thereafter, the coupler 42 is rotated so that the female screw on the coupler 42 will be firmly meshed with the male screw on the drum-side base 46. Consequently, electrically coupling the endoscope 3 to the drum 4 and joining the fluid tubes with the fluid coupling members are completed readily and reliably.

If each connector has an alignment pin and alignment groove, alignment can be achieved more readily.

Figure 7:
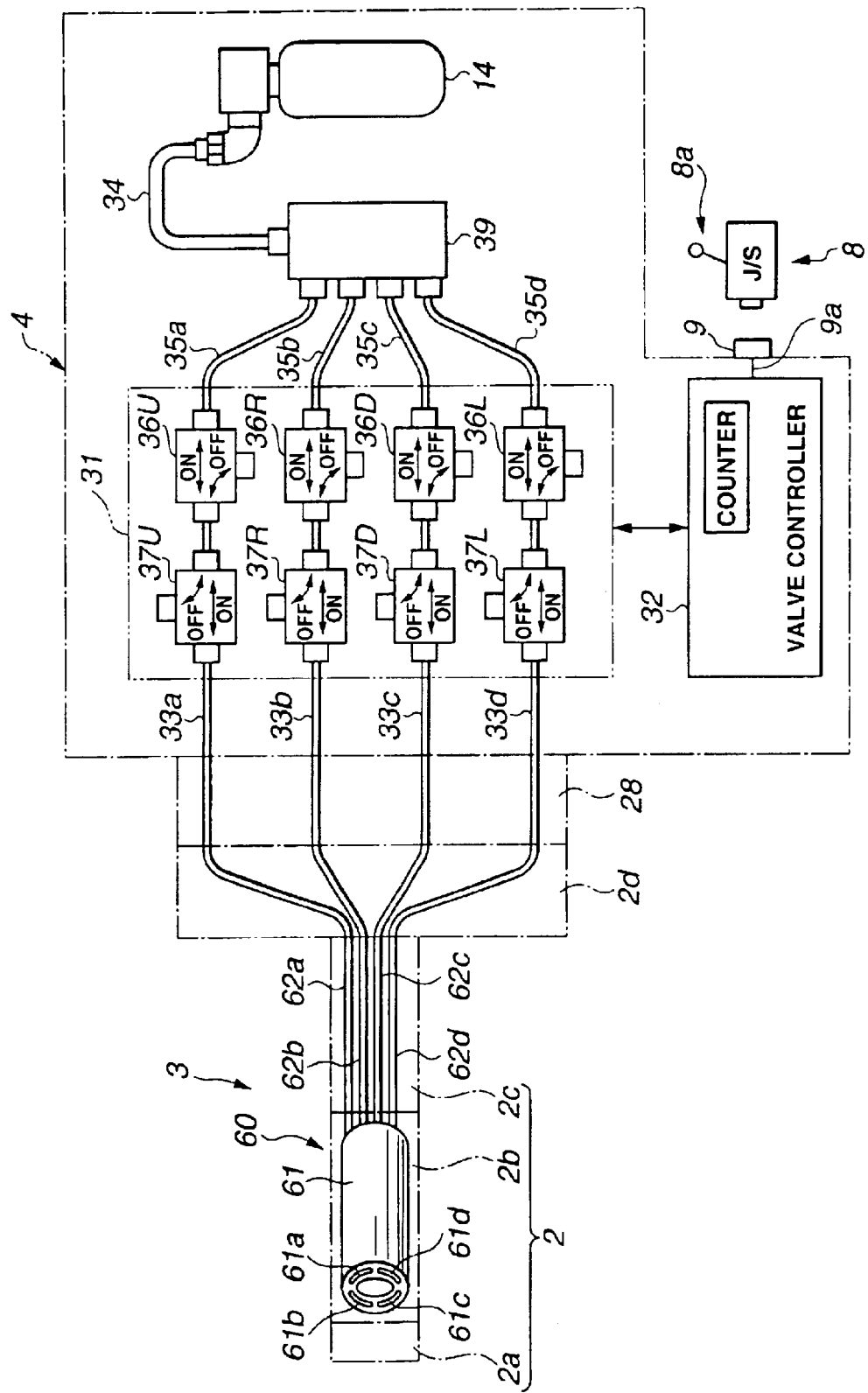
FIG. 7 is an explanatory block diagram showing the configuration of a major portion of the endoscopic apparatus.

As shown in FIG. 7, the bending section 2b has a multi-lumen tube 61 that is included in a fluid-pressure actuator 60. The multi-lumen tube 61 is made of, for example, a soft silicon material, and has four penetrating holes 61a, 61b, 61c, and 61d formed circumstantially. A center through hole 61e is formed in the center of the multi-lumen tube 61. The penetrating holes 61a, 61b, 61c, and 61d serve as our fluid chambers associated with the bending directions in which the bending section 2b can be bent, for example, upward, downward, rightward, and leftward directions.

The distal parts of insertion unit-side fluid supply tubes (hereinafter abbreviated to insertion unit-side tubes) 62a, 62b, 62c, and 62d over which fluid is supplied and which are made of, for example, Teflon (registered trademark) are joined with the proximal parts of the four penetrating holes 61a, 61b, 61d, and 61d respectively. The proximal parts of the insertion unit-side tubes 62a, 62b, 62c, and 62d are joined with the fluid coupling members 45 of the endoscope-side connector 2d.

A cylinder pipe 34 over which gas is supplied from the gas cylinder 14 is coupled to a tube coupling 39. The ends of four control-side fluid supply tubes (hereinafter abbreviated to control-side tubes) 35a, 35b, 35c, and 35d associated with the four bending directions, that is, the upward, downward, rightward, and leftward directions are coupled to the tube coupling 39. The other ends of the control-side tubes 35a, 35b, 35c, and 35d are coupled to cylinder-side electromagnetic valves 36U, 36D, 36L, and 36R associated with the respective bending directions. The cylinder-side electromagnetic valves 36U, 36D, 36L, and 36R are included in the valve unit 31.

On the other hand, the proximal ends of the fluid supply tubes 33a, 33b, 33c, and 33d that extend from the drum-side connector 28 and that are associated with the respective bending directions are coupled to connector-side electromagnetic valves 37U, 37D, 37L, and 37R associated with the respective bending directions. The connector-side electromagnetic valves 37U, 37D, 37L, and 37R are included in the valve unit 31. The connector-side electromagnetic valves 37U, 37D, 37L, and 37R communicate with the cylinder-side electromagnetic valves 36U, 36D, 36L, and 36R via respective tubes.

Consequently, when the endoscope-side connector 2d and drum-side connector 28 are joined with each other, the electromagnetic valves 36U, 36D, 36L, 36R, 37U, 37D, 37L, and 37R included in the valve unit 31 are opened or closed by appropriately handling the joystick 8a included in the remote controller 8. Consequently, the gas in the gas cylinder 14 is fed into the fluid chambers realized with the penetrating holes 61a, 61b, 61c, and 61d by way of the cylinder pipe 34, control-side tubes 35a, 35b, 35c, and 35d, valve unit 31, fluid supply tubes 33a, 33b, 33c, and 33d, and insertion unit-side tubes 62a, 62b, 62c, and 62d. Eventually, the bending section 2b is bent responsively to the handling of the joystick 8a.

Now, an example of a procedure for constructing the fluid-pressure actuator 60 will be described below.

Figure 8:
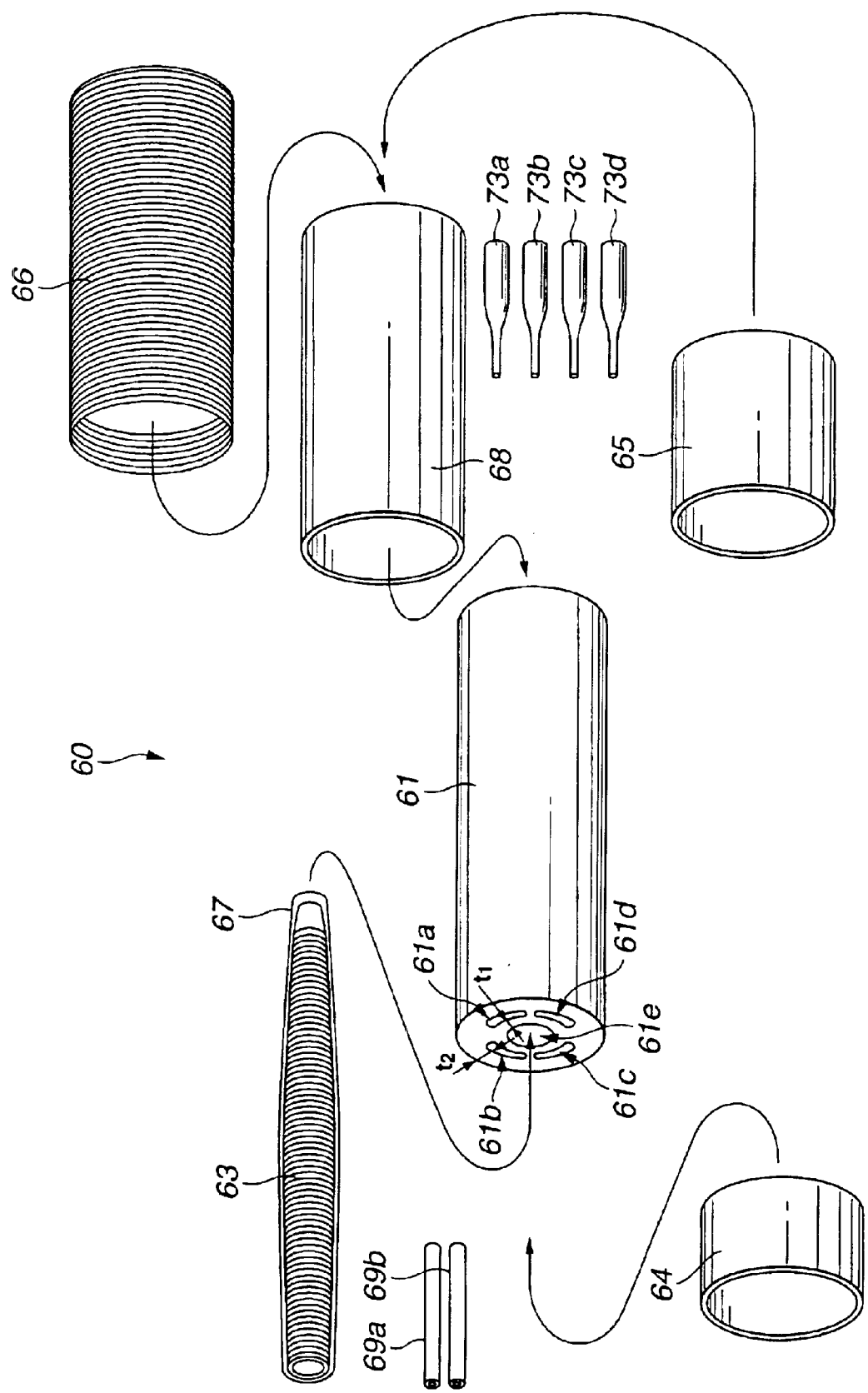
FIG. 8 is an explanatory diagram showing the members constituting the fluid-pressure actuator and the relationships among them.

To begin with, as shown in FIG. 8, an internal coil 63 that is an internal tubular member is sheathed with an inner thin tube 67. The internal coil 63 is put in the center through hole 61e. At this time, a first exhaust tube 69a that is a tubular body is interposed as an exhaust discharging means between the distal part of the center through hole 61e and the inner thin tube 67.

Figure 9A:
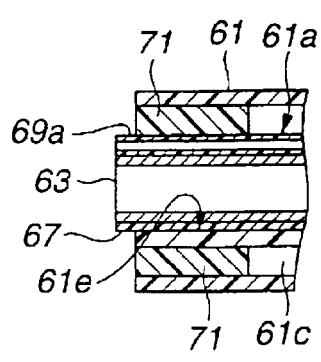
FIG. 9A is an explanatory diagram concerning a step of forming a first adhesive portion.
Figure 9B:
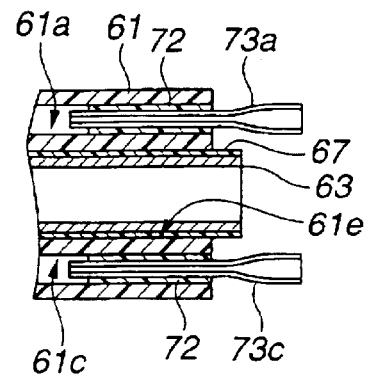
FIG. 9B is an explanatory diagram concerning a step of forming a second adhesive portion.

Thereafter, as shown in FIG. 9A, for example, a silicon adhesive is poured into the distal parts of the penetrating holes 61a, 61b, 61c, and 61d of the multi-lumen tube 61 in order to form a first adhesive portion 71 that blocks the distal openings of the penetrating holes. Moreover, as shown in FIG. 9B, a second adhesive portion 72 that blocks the proximal openings of the penetrating holes 61a, 61b, 61c, and 61d is formed. Prior to the formation of the second adhesive portion 72, communication members 73a, 73b, 73c, and 73d are inserted in the penetrating holes.

Consequently, the penetrating holes 61a, 61b, 61c, and 61d of the multi-lumen tube 61 are reformed into spaces by means of the first and second adhesive portions 71 and 72. Moreover, the spaces communicate with outside via the communication members 73a, 73b, 73c, and 73d respectively, whereby fluid chambers are completed.

Figure 9C:
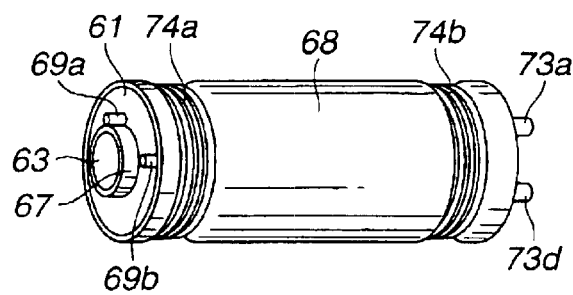
FIG. 9C is an explanatory diagram concerning a step of forming a bobbin adhesive portion.

Thereafter, as shown in FIG. 9C, an outer thin tube 68 is put on the periphery of the multi-lumen tube 61. At this time, a second exhaust tube 69b that is a tubular body is interposed as an exhaust discharging means between the distal part of the multi-lumen tube 61 and the outer thin tube 68.

Thereafter, a bobbin adhesive portion 74a is formed on each of the distal and proximal parts of the multi-lumen tube 61 sheathed with the outer thin tube 68. Consequently, the exhaust tubes 69a and 69b located in the distal part of the multi-lumen tube are fixed at predetermined positions. Near the bobbin adhesive portions 74a, the inner thin tube 67 sheathing the internal coil 63 and the multi-lumen tube 61, and the outer thin tube 68 and the multi-lumen tube 61 come into close contact with each other.

Incidentally, before the multi-lumen tube 61 is sheathed with the outer thin tube 68, the communication members 73a, 73b, 73c, and 73d may be inserted into the penetrating holes 61a, 61b, 61c, and 61d of the multi-lumen tube 61 and then secured using an adhesive. Thereafter, a thread-tying portion may be formed on a portion of the periphery of the multi-lumen tube 61 inside which the communication members 73a, 73b, 73c, and 73d are located. Finally, the outer thin tube 68 and multi-lumen tube 61 may be secured as an integrated body using an adhesive with a bobbin adhesive portion 74b on the proximal parts.

Figure 9D:
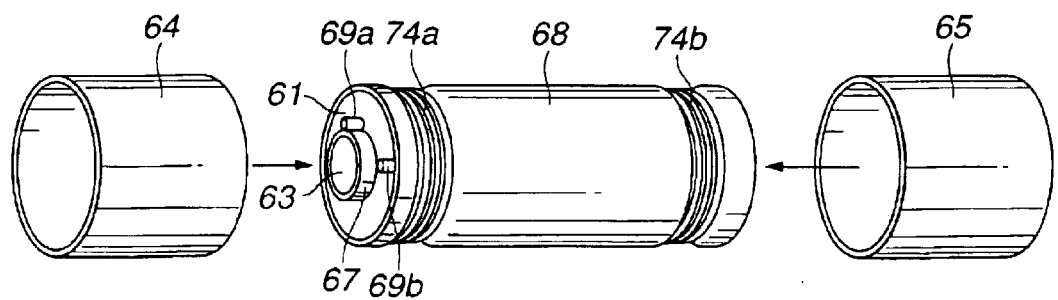
FIG. 9D is an explanatory diagram concerning a step of attaching bases.

Thereafter, as shown in FIG. 9D, a front base 64 serving as a gap formation member is attached to the distal end of the multi-lumen tube 61 sheathed with the outer thin tube 68. A rear base 65 serving as a gap formation member is attached to the proximal end of the multi-lumen tube 61 sheathed with the outer thin tube 68.

Figure 10:
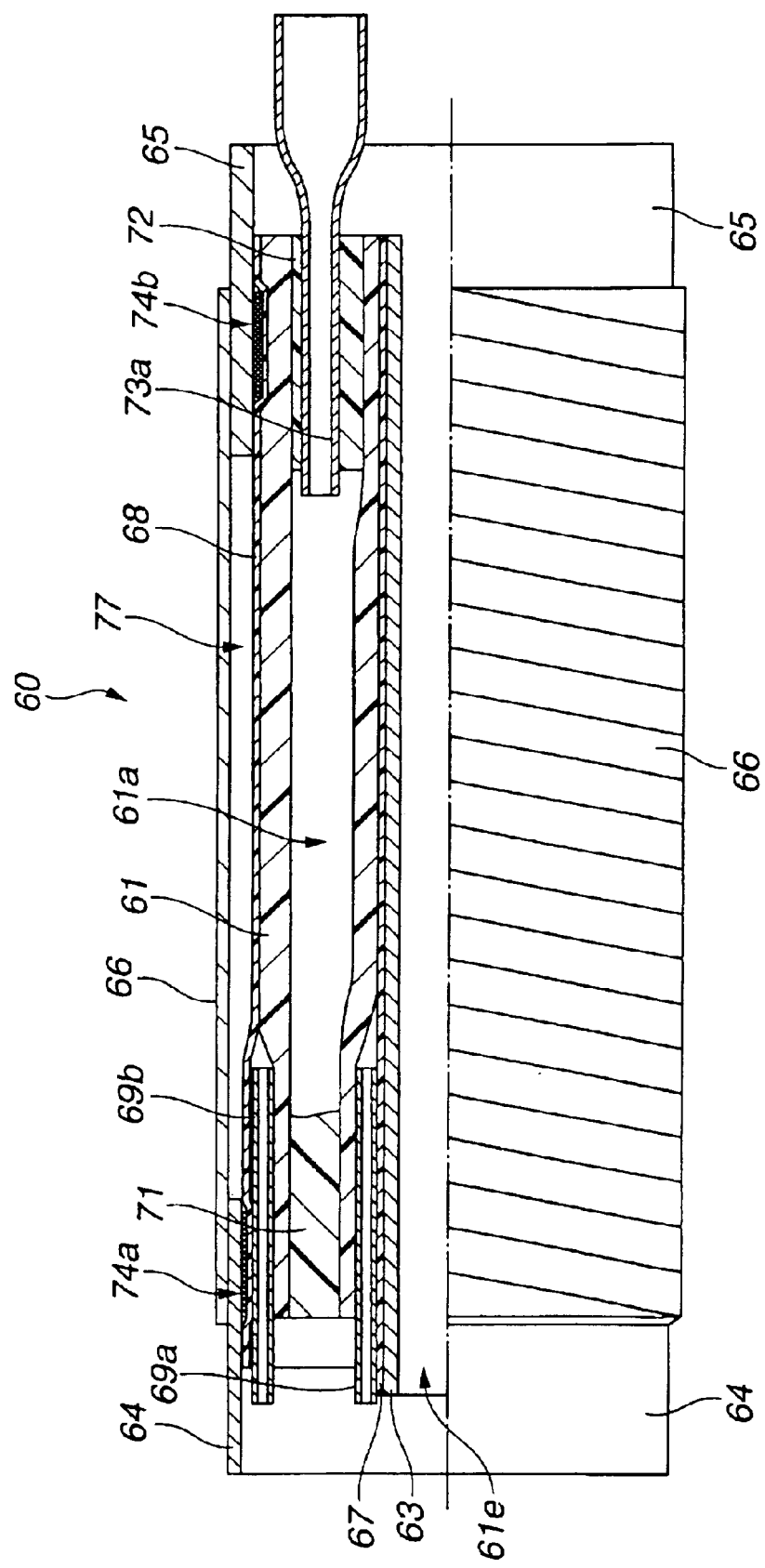
FIG. 10 is an explanatory diagram showing the structure of the fluid-pressure actuator.

Thereafter, an external coil 66 that is an external tubular member is put on the periphery of the multi-lumen tube 61 sheathed with the outer thin tube 68. At this time, the distal part of the external coil 66 is put on the periphery of the front base 64, and the proximal part thereof is put on the periphery of the rear base 65. This results in the fluid-pressure actuator 60 that has, as shown in FIG. 10, a gap 77 created between the outer thin tube 68 and external coil 66.

The gap 77 allows the fluid chambers to axially stretch and radially slightly expand during pressurization during which fluid is supplied. This helps ease bending.

In the foregoing fluid-pressure actuator 60, if the gas in the fluid chambers leaks out between the multi-lumen tube 61 and the outer thin tube 68, the leaking air is discharged to outside over the exhaust tube 69b sandwiched between the multi-lumen tube 61 and outer thin tube 68. Moreover, if the gas in any of the fluid chambers leaks out between the multi-lumen tube 61 and inner thin tube 67, the leaking air is discharged to outside over the exhaust tube 69a sandwiched between the multi-lumen tube 61 and inner thin tube 67.

Namely, even if gas leaks out between the multi-lumen tube 61 and outer thin tube 68 or between the multi-lumen tube 61 and inner thin tube 67, the gas is prevented from staying in the fluid-pressure actuator 60.

As mentioned above, a fluid-pressure actuator is constructed with a thin tube sandwiched between a multi-lumen tube which has penetrating holes serving as fluid chambers, and a coil which restricts expansion of the multi-lumen tube. Herein, the thin tube prevents part of the expanding multi-lumen tube from being caught by adjoining ones of the turns of the coil, projecting, and thus being damaged. At this time, at least one exhaust tube is sandwiched between the thin tube and multi-lumen tube. Consequently, even if gas leaks out of any of the penetrating holes of the multi-lumen tube into the sealed gap between the thin tube and multi-lumen tube, the gas leaking into the gap between the thin tube and multi-lumen tube can be discharged to outside the fluid-pressure actuator over the exhaust tube.

Consequently, the drawback that the gas leaking out of any of the fluid chambers of the multi-lumen tube included in the fluid-pressure actuator stays between the thin tube and multi-lumen tube and becomes the resistance to bending of the bending section to change a degree of bending can be avoided reliably.

Incidentally, the exhaust discharging means is not limited to the exhaust tubes 69a and 69b sandwiched between the multi-lumen tube 61 and thin tube 67 or 68, but may have the structures shown in FIG. 11A to FIG. 12C.

Figure 11A:
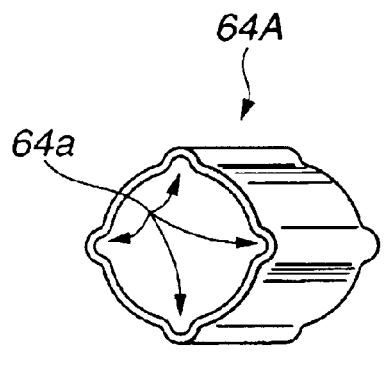
FIG. 11A is an explanatory diagram showing an example of the structure of a front base.
Figure 11B:
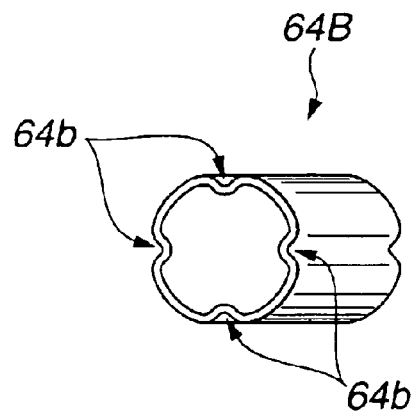
FIG. 11B is an explanatory diagram showing another example of the structure of the front base.

Referring to FIG. 11A and FIG. 11B, pluralities of exhaust channels 64a and 64b are formed as the exhaust discharging means in the front base 64A or 64B.

Figure 11C:
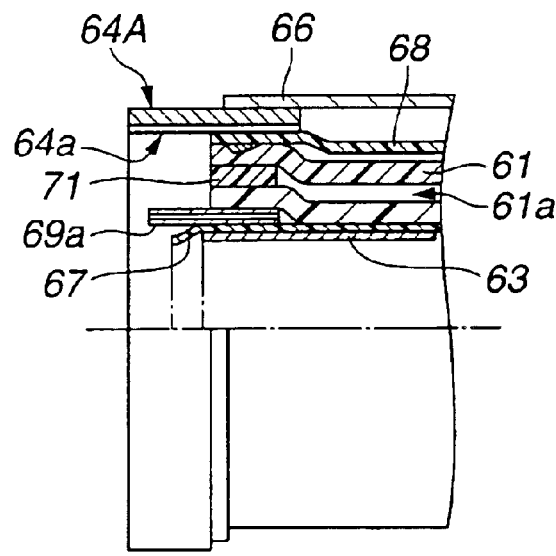
FIG. 11C is an explanatory diagram concerning the operation of the front base shown in FIG. 11A.

Specifically, as shown in FIG. 11C, the front base 64A is attached to the periphery of the multi-lumen tube 61 sheathed with the outer thin tube 68. In this state, if gas leaks out and stays between the outer thin tube 68 and the multi-lumen tube 61, the staying gas is discharged to outside from between the thin tube 68 and multi-lumen tube 61 that are not in close contact with each other due to the exhaust channels 43a of the front base 64A. Consequently, the same operation and advantages as those of the foregoing embodiment can be provided.

Figure 11D:
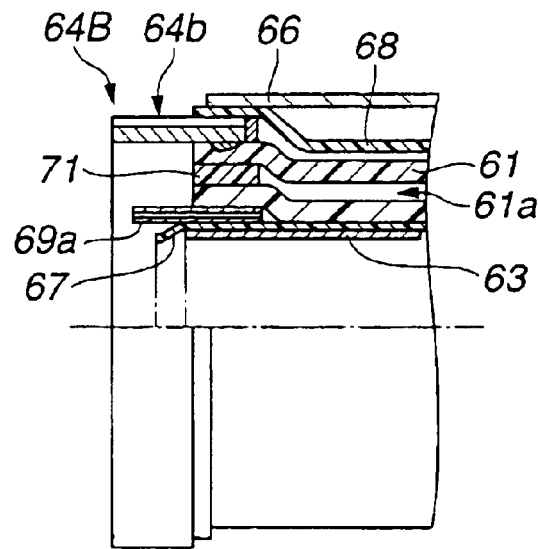
FIG. 11D is an explanatory diagram concerning the operation of the front base shown in FIG. 11B.

On the other hand, as shown in FIG. 11D, the front base 64A or 64B is attached to the periphery of the multi-lumen tube 61, and has the periphery thereof sheathed with the outer thin tube 68. In this case, if gas leaks out and stays between the outer thin tube 68 and multi-lumen tube 61, the staying gas is discharged to outside through the exhaust channels 64a or 64b of the front base 64A or 64B. Consequently, the same operation and advantages as those of the aforesaid embodiment can be provided.

Incidentally, the exhaust channels 64a and 64b may be formed in the rear base 65.

Figure 12A:
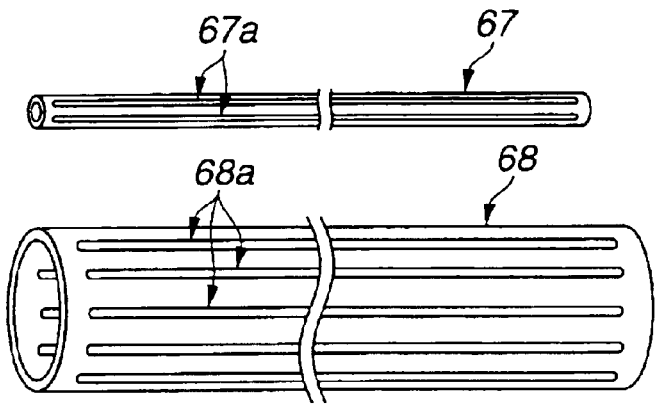
FIG. 12A is an explanatory diagram showing thin tubes having slits.
Figure 12B:
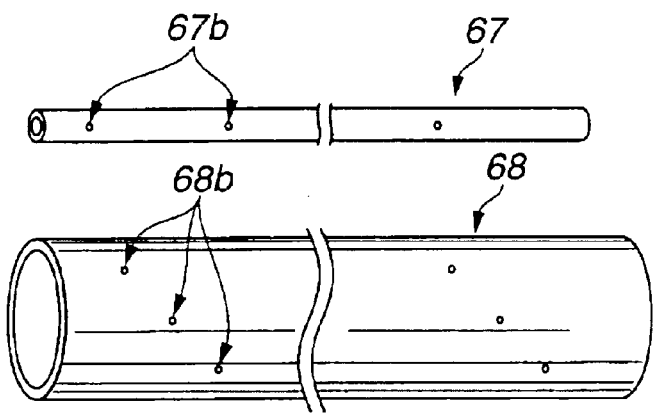
FIG. 12B is an explanatory diagram showing thin tubes having exhaust holes.
Figure 12C:
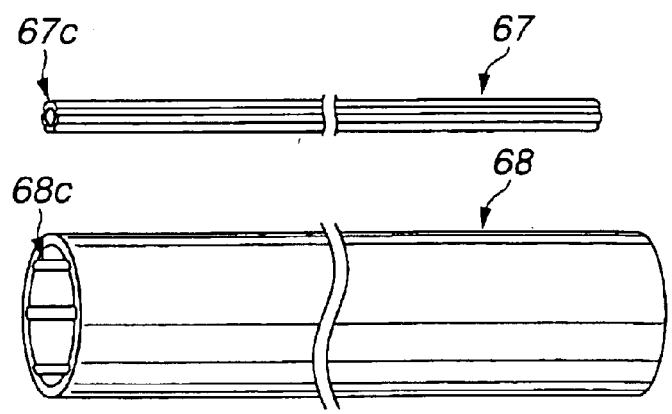
FIG. 12C is an explanatory diagram showing thin tubes having an uneven part.

Referring to FIG. 12A to FIG. 12C, the exhaust discharging means is formed directly in the thin tubes 67 and 68.

Specifically, referring to FIG. 12A, the inner thin tube 67 and outer thin tube 68 have as the exhaust discharging means at least one slit 67a or 68a that serves as an exhaust channel. Referring to FIG. 12B, the inner thin tube 67 and outer thin tube 68 have as the exhaust discharging means at least one exhaust hole 67b or 68b that links the outside and inside of the thin tube 67 or 68.

Referring to FIG. 12C, the inner thin tube 67 has as the exhaust discharging means an uneven part 46c extended on the periphery thereof in the longitudinal direction thereof. The outer thin tube 68 has as the exhaust discharging means an uneven part 47c extended on the internal surface thereof in the longitudinal direction thereof.

Consequently, if gas leaks out between the thin tube 67 or 68 and the multi-lumen tube 61, the gas staying between the thin tube 67 or 68 and the multi-lumen tube 61 is discharged to outside through the slits 67a or 68a, the exhaust holes 67b or 68b, or the dent portion of the uneven part 67c or 68c. Consequently, the same operation and advantages as those of the aforesaid embodiment can be provided. Incidentally, the thin tubes 67 and 68 may be formed with porous members, through which gas permeates, in order to provide the same operation and advantages.

According to the present embodiment, the multi-lumen tube 61 has the four penetrating holes 61a, 61b, 61c, and 61d regularly arranged around the center through hole 61e. However, the number of penetrating holes in the multi-lumen tube is determined based on the bending directions and a shape in which the bending section should be bent. Therefore, the number of penetrating holes is not limited to four but may be four or more or less.

In the process of forming the penetrating holes 61a, 61b, 61c, and 61d, a distance t1 from the wall of the center through hole to the internal side of the wall of each penetrating hole, and a distance t2 from the external side of the wall of each penetrating hole to the periphery of the multi-lumen tube are determined to have a relationship of t1<t2.

Next, the structure of the flexible tube formation member that is coupled to the fluid-pressure actuator 60 will be described below.

Figure 13:
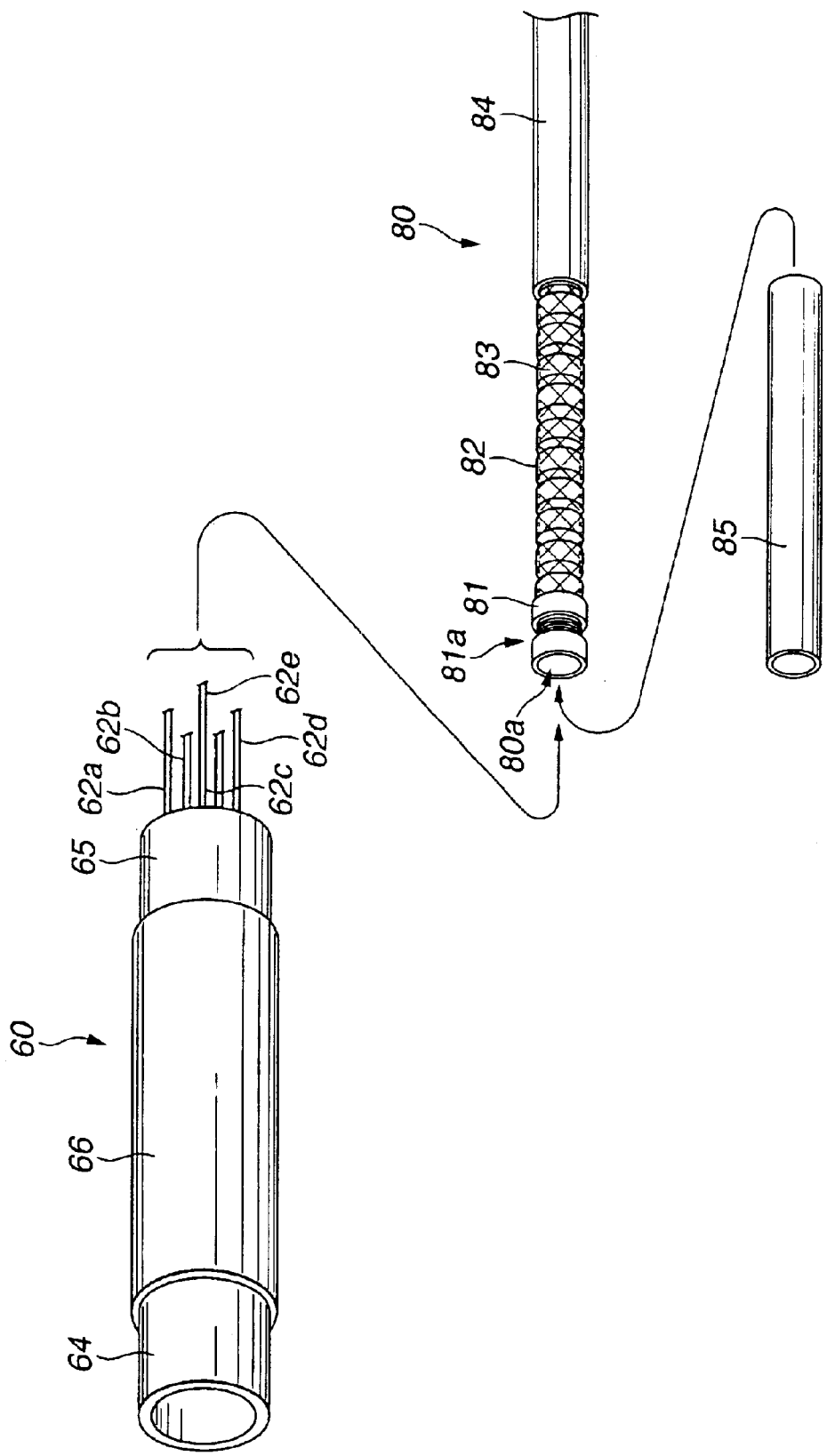
FIG. 13 is a diagram for explaining the structure of a flexible tube formation member coupled to the fluid-pressure actuator.

As shown in FIG. 13, a distal flexible-tube base 81 included in a flexible tube formation member 80 that forms the flexible tube 2c is firmly joined with the rear base 65 serving as the proximal part of the fluid-pressure actuator 60.

Specifically, the flexible tube formation member 80 comprises the distal flexible-tube base 81, a helical pipe 82, a metallic braided pipe 83, a rear resin tube 84, and a front resin tube 85.

The helical pipe 82 is elongated by helically winding a belt-like thin metallic plate member one-fold, twofold, or threefold. The distal flexible-tube base 81 is disposed at the distal end of the helical pipe 82. The metallic braided pipe 83 sheathes the helical pipe 82. The rear resin tube 84 sheathes the metallic braided pipe 83, which sheathes the helical pipe 82, from the proximal end to the distal end thereof. The front resin tube 85 sheathes the front side of the helical pipe 82 sheathed with the metallic braided pipe 83.

The flexibility of the front resin tube 85 is determined so that the front resin tube 85 will be soft enough to be bent with a weaker load than the rear resin tube 84 is. Consequently, the flexibility of the flexible tube formation member 80 is determined so that the front side of the flexible tube formation member 80 will be softer than the rear side thereof. Therefore, the flexible tube formation member 80 can be thrust into a deep region more smoothly.

A circumferential groove 81a is formed in the middle of the distal flexible-tube base 81. An O ring (reference numeral 86 in FIG. 14A) that provides predetermined constraining force, serves as a fastening member, and keeps the joint between the rear base 65 and the distal flexible-tube base 81 watertight is locked in the circumferential groove 81a. Reference numeral 62e denotes a signal cable extending from a C-MOS that is not shown. The signal cable 62e runs through the lumen 80a of the flexible tube formation member 80 to reach the endoscope-side connector 2d together with the insertion unit-side tubes 62a, 62b, 62c, and 62d.

As shown in FIG. 14A, the distal flexible-tube base 81 serving as the distal part of the flexible tube formation member 80 is thrust into a predetermined position in the rear base 65 of the fluid-pressure actuator 60 against the constraining force provided by the O ring 86. Consequently, the O ring 86 comes into close contact with the internal surface of the rear base 65. Eventually, the joint between the distal flexible-tube base 81 and rear base 65 is kept watertight. Moreover, the distal flexible-tube base 81 and rear base 65 are firmly integrated with each other owing to the constraining force of the O ring 86. Namely, the fluid-pressure actuator 60 and flexible tube formation member 80 are coupled to each other.

As shown in FIG. 14A, the peripheries of the fluid-pressure actuator 60 and flexible tube formation member 80 that are coupled to each other are sheathed with an insertion unit cover 94a shown in FIG. 14B or an insertion unit cover 94b shown in FIG. 14C. This results in the insertion unit 2.

The insertion unit cover 94a comprises a first bending cover 91 formed with a metallic braid that is longer by ΔL than the length L of the fluid-pressure actuator 60, and a flexible tube cover 93 formed with a metallic braid having a predetermined dimension. The inner diameter of the first bending cover 91 is substantially identical to the outer diameter D of the fluid-pressure actuator 60.

The insertion unit cover 94b comprises a second bending cover 92 formed with a metallic braid whose length is identical to the length L of the fluid-pressure actuator 60, and a flexible tube cover 93 formed with a metallic braid having a predetermined dimension. The inner diameter of the second bending cover 92 is larger by ΔD from the outer diameter D of the fluid-pressure actuator 60.

In case the insertion unit cover 94a is put on the fluid-pressure actuator 60 and flexible tube formation member 80, the first bending cover 91 having the length L+ΔL is compressed to have the length L. The both ends of the first bending cover 91 are then attached to the front base 64 and rear base 65 respectively.

Figure 15:
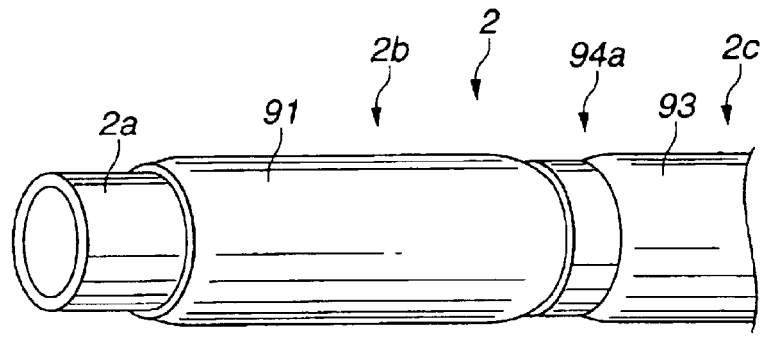
FIG. 15 is a perspective view showing the distal part of the insertion unit.

This results in, as shown in FIG. 15, the insertion unit 2 sheathed with the insertion unit cover 94a. In the insertion unit 2, the first bending cover 91 is compressed to have the length L. Therefore, the middle of the first bending cover 91 bulges and dilates compared with the both ends thereof.

Figure 16A:
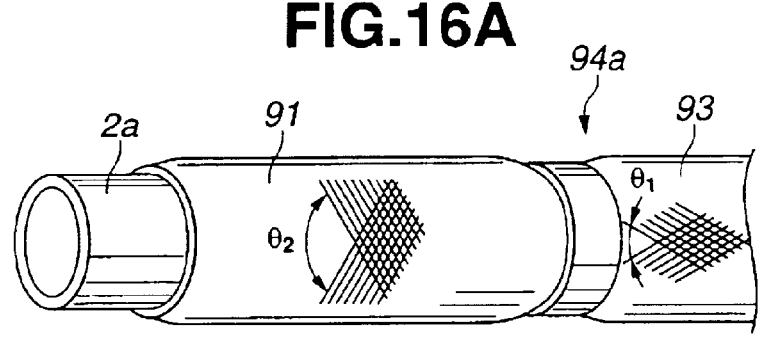
FIG. 16A is an explanatory diagram showing a difference in an angle, at which braided strands meet, between the bending cover and flexible tube cover.
Figure 16B:
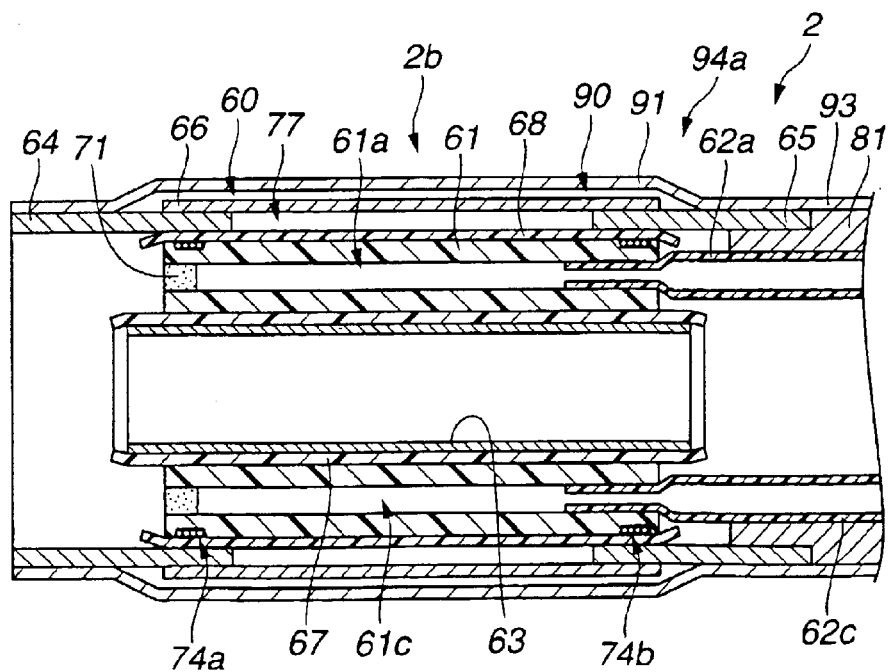
FIG. 16B is a sectional view showing the structure of a bending section included in the insertion unit.

Consequently, as shown in FIG. 16A, an angle θ1 at which the strands woven into the first bending cover 91 meets changes to an angle θ2. Herein, the angle θ1 is identical to the angle at which the strands woven into the metallic braid forming the flexible tube cover 93. On the other hand, as shown in FIG. 16B, in the inside of the bending section 2b, a gap 90 is created between the first bending cover 91 and the external coil 66 included in the fluid-pressure actuator 60.

Incidentally, the insertion unit cover 94b may be put on the fluid-pressure actuator 60 and flexible tube formation member 80, and both ends of the second bending cover 92 may be attached to the front base 64 and rear base 65. In this case, the diameter of the second bending cover 92 included in the insertion unit cover 94b is larger by ΔD. Therefore, substantially like the structure of the bending section 2b sheathed with the insertion unit cover 94a as shown in FIG. 16B, the gap 90 is created between the external coil 66 and second bending cover 92.

Now, an example of a method of fixing the bending cover 91 or 92 and the flexible tube cover 93, which constitutes the insertion unit cover 94a or 94b, to the fluid-pressure actuator 60 will be described with reference to drawings below.

As shown in FIG. 17A, a female screw 101 is threaded at predetermined positions on each of the front base 64 and rear base 65 included in the fluid-pressure actuator 60. A first coupling 103 is fixed to each of the distal part and proximal part of the first or second bending cover 91 or 92. A penetrating hole 102 into which a locking screw meshed with the female screw 101 is fitted is, as shown in FIG. 17B and FIG. 17C, formed at predetermined positions on each of the first couplings 103. Moreover, as shown in FIG. 17D, a second coupling 105 is fixed to the distal part of the flexible tube cover 93. A penetrating hole 104 into which a locking screw meshed with the female screw 101 is inserted is formed at predetermined positions in the second coupling 105.

First, the penetrating holes 104 formed in the second coupling 105 fixed to the flexible tube cover 93 are aligned with the predetermined female screws 101 formed in the rear base 65. A locking screw that is not shown is fitted into each of the female screws 101 through each of the penetrating holes 104. Consequently, the flexible tube cover 93 is firmly integrated with the rear base 65.

Thereafter, the penetrating holes 102 formed in the coupling 103 fixed to the proximal part of the first or second bending cover 91 or 92 are aligned with the predetermined female screws 101 formed in the rear base 65. A locking screw that is not shown is then fitted into each of the female screws 101 through each of the penetrating holes 102.

Thereafter, the penetrating holes 102 formed in the coupling 103 fixed to the distal part of the first or second bending cover 91 or 92 are aligned with the female screws 102 formed in the front base 64. A locking screw that is not shown is then fitted into each of the female screws 101 through each of the penetrating holes 102. Consequently, the bending cover 91 or 92 is firmly integrated with the front base 64 and rear base 65 included in the fluid-pressure actuator 60.

As mentioned above, the insertion unit cover 94a or insertion unit cover 94b is secured to the fluid-pressure actuator 60 with which the flexible tube formation member 80 is integrated, whereby the insertion unit 2 is completed.

The operation of the endoscopic apparatus 1 having the foregoing components will be described below.

Figure 18A:
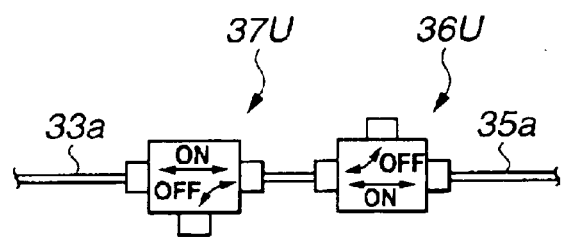
FIG. 18A is an explanatory diagram concerning the operations of a cylinder-side electromagnetic valve and a connector-side electromagnetic valve that are associated with an upward direction.

In order to angle the bending section 2b in an upward direction, the joystick 8a of the remote controller 8 is tilted in a predetermined direction from a neutral position. Consequently, a bending directive signal is transmitted from the joystick 8a to the valve controller 32. In response to the bending directive signal, the valve controller 32 controls the cylinder-side electromagnetic valve 36U and connector-side electromagnetic valve 37U that are associated with the angling in the upward direction as shown in FIG. 18A.

When the joystick 8a is handled in order to bend the bending section in the upward direction, the electromagnetic valves 36U and 37U are intermittently repeatedly opened or closed at the same time. Consequently, only when the electromagnetic valves 36U and 37U communicate with each other as indicated with an arrow ON, nitrogen in the gas cylinder 14 passes through the electromagnetic valves 36U and 37U and flows into the fluid chamber associated with the bending in the upward direction.

Figure 19A:
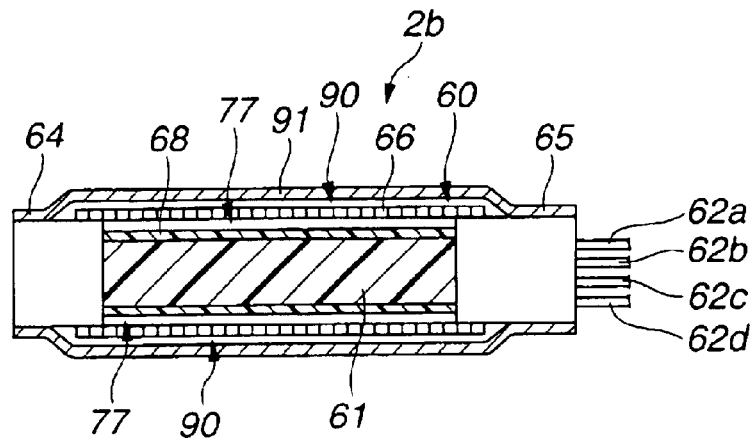
FIG. 19A shows the bending section that has not yet bent.

Consequently, the predetermined fluid chamber of the linear fluid-pressure actuator 60 that is associated with the bending in the upward direction is gradually pressurized as shown in FIG. 19A.

Figure 19B:
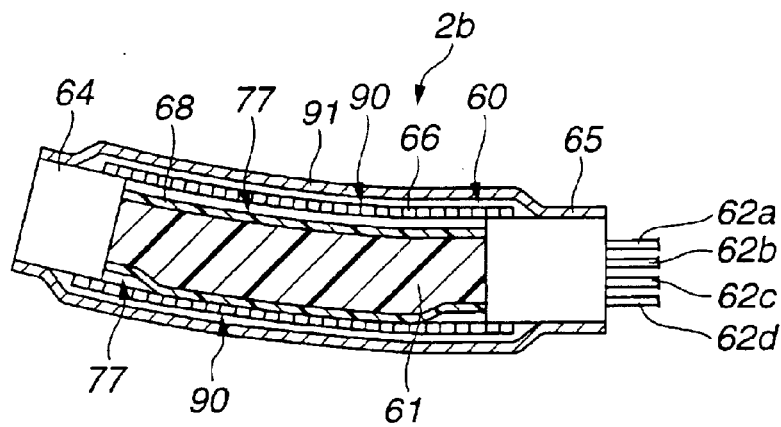
FIG. 19B shows the bending section that has started bending.

Thereafter, as more nitrogen is supplied to the fluid chamber, the multi-lumen tube 61 with which the outer tube 68 is in close contact expands, as shown in FIG. 19B, without any change in the length thereof so that the gap 77 will be nullified. The multi-lumen tube 61 then abuts on part of the external coil 66, and the bending section 2b starts bending.

Thereafter, as more nitrogen is supplied to the fluid chamber, the multi-lumen tube 61 sheathed with the outer tube 68 expands and stretches axially. Consequently, the multi-lumen tube 61-causes the bending section 2b to bend while being in close contact with the external coil 66. At this time, the bending section 2b bends without bringing the external coil 66 and bending cover 91 into contact with each other.

Figure 19C:
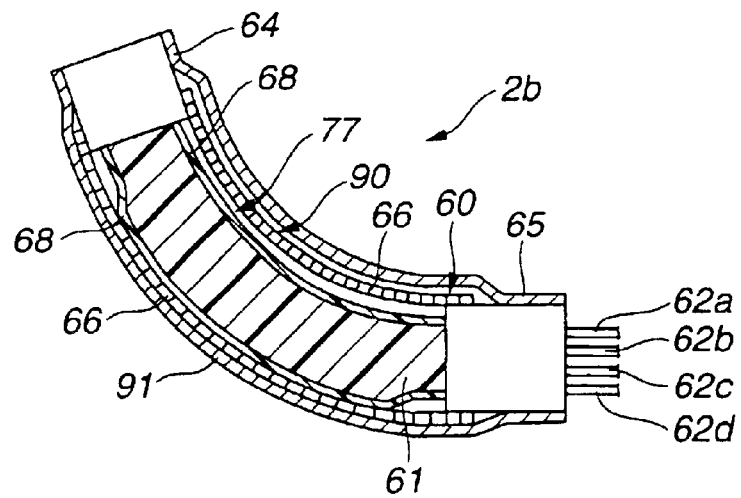
FIG. 19C shows the maximally bent state of the bending section.

As shown in FIG. 19C, when the gap 90 between the external coil 66 and bending cover 91 becomes nil, that is, when the external coil 66 substantially abuts on the bending cover 91, the bending section 2b enters the maximally bent state.

Incidentally, the repetition frequency by which the electromagnetic valves 36U and 37U repeat the opening/closing motion is controlled using a counter according to an angle at which the joystick 8a is tilted. Consequently, excessive supply of fluid into the fluid chamber is prevented. Moreover, excessive bending of the bending section 2b is avoided. Occurrence of a defect in the fluid-pressure actuator 60 included in the bending section 2b is prevented.

Moreover, the electromagnetic valves 36U and 37U are simultaneously brought to a communicating state indicated with the arrow ON or to an occluded state indicated with an arrow OFF simultaneously at regular intervals. Consequently, when the electromagnetic valves 36U and 37U are brought to the state indicated with the arrow OFF, nitrogen supplied to the fluid chamber during fluid supply stays in the fluid chamber but will not be discharged from the electromagnetic valves 36U and 37U.

Next, a description will be made of a case where the joystick 8a is returned from the position at which the bending in the upward direction is directed back to the neutral position.

Figure 18B:
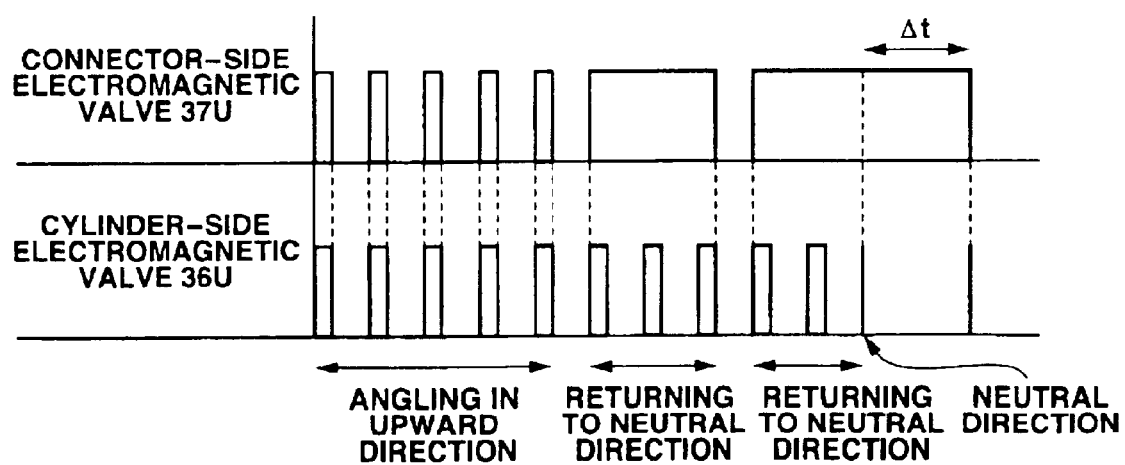
FIG. 18B is an explanatory diagram showing an example of the opening/closing motions of the cylinder-side electromagnetic valve and connector-side electromagnetic valve.

At this time, the valve controller 32 transmits a directive signal to the electromagnetic valves 36U and 37U. Consequently, as indicated in FIG. 18B, the connector-side electromagnetic valve 37U is controlled to enter the state indicated with the arrow ON for a predetermined period of time. Moreover, the cylinder-side electromagnetic valve 36U is intermittently opened or closed.

Namely, while the connector-side electromagnetic valve 37U is brought to the communicating state, if the cylinder-side electromagnetic valve 36U is intermittently repeatedly opened or closed, the nitrogen supplied to the fluid chamber is gradually discharged to outside through the cylinder-side electromagnetic valve 36U. Consequently, for example, the maximally bent state of the bending section 2b shown in FIG. 19C gradually changes to a moderately bent state.

Thereafter, if the joystick 8a is returned from the position at which the bending in the upward direction is directed back to the neutral position, the valve controller 32 transmits a directive signal to the electromagnetic valves 36U and 37U. Consequently, as shown in FIG. 18B, the connector-side electromagnetic valve 37U is controlled to enter the state indicated with the arrow ON for a predetermined period of time, and the cylinder-side electromagnetic valve 3U is intermittently opened or closed. Namely, the nitrogen supplied to the fluid chamber is discharged to outside through the cylinder-side electromagnetic valve 36U. The bent state of the bending section 2b bent to a predetermined degree in the upward direction by means of the fluid-pressure actuator 60 changes to a neutral state.

According to the present invention, the first bending cover 91 is mounted while being compressed. Therefore, force exerted in returning the angle, at which strands woven into a metallic braid forming the first bending cover 91 meets, from θ2 to θ1 is working all the time. Consequently, when the force exerted in returning the angle, at which strands woven into the metallic braid forming the first bending cover 91 meets gets larger than a load imposed by the fluid-pressure actuator 60, the bending section 2b smoothly makes a transition to a linear state.

Moreover, when the joystick 8a is moved to lie at an intermediate position between the positions at which the bending in the upward direction and the bending in the rightward direction are directed, the valve controller 32 transmits a directive signal to the cylinder-side electromagnetic valves 36U and 36R associated with the bending in the upward direction and to the connector-side electromagnetic valves 37U and 37R associated with the bending in the rightward direction.

Consequently, the nitrogen in the gas cylinder 14 is fed to the fluid chamber associated with the bending in the upward direction and to the fluid chamber associated with the bending in the rightward direction. Eventually, the bending section 2b is bent in an intermediate direction of the upward and rightward directions.

When the joystick 8a is returned from the position, at which the bending in the intermediate direction of the upward and rightward directions is directed, back to the neutral position, the valve controller 32 transmits a directive signal to the cylinder-side electromagnetic valves 36U and 36R and the connector-side electromagnetic valves 37U and 37R which are associated with the upward and rightward directions respectively. Consequently, the nitrogen supplied to each of the fluid chamber associated with the bending in the upward direction and the fluid chamber associated with the bending in the rightward direction is discharged to outside through the cylinder-side electromagnetic valves 36U and 36R. The bent state of the bending section changes to a slightly bent state.

The relationship between the tilting of the joystick 8a to a position associated with any other direction and the actions of the cylinder-side electromagnetic valve and connector-side electromagnetic valve responsive to the tilting is identical to the one established when the joystick is tilted to the position associated with the bending in the rightward direction or to the position associated with the bending in the intermediate direction of the upward and rightward directions. The description of the relationship will therefore be omitted.

As mentioned above, the gap is created between the multi-lumen tube sheathed with the outer tube and the external coil. Therefore, when fluid is supplied to any of the fluid chambers, the multi-lumen tube included in the fluid-pressure actuator temporarily expands to slightly bend. Thereafter, the multi-lumen tube stretches axially and allows the bending section to smoothly bend.

Consequently, the multi-lumen tube included in the fluid-pressure actuator smoothly shifts actions to stretch axially without incurring a large load. Consequently, a drawback such as the fatigue of the fluid-pressure actuator is prevented to improve the durability of the fluid-pressure actuator.

Moreover, the gap is created between the fluid-pressure actuator included in the bending section and the bending cover. Therefore, when fluid is supplied to any of the fluid chambers included in the fluid-pressure actuator, the bending section starts bending. At this time, the external coil included in the fluid-pressure actuator is prevented from touching the metallic braid that serves as the bending cover. Therefore, when the bending section is bent, a defect attributable to the fact that the metallic braid is caught between adjoining ones of the turns of the external coil can be resolved. Namely, the performance of the endoscopic apparatus in terms of bending improves.

Furthermore, in the process of constructing the multi-lumen tube, the distance t1 from the wall of the center through hole to the internal side of the wall of each penetrating hole, and the distance t2 from the external side of the wall of each penetrating hole to the periphery of the multi-lumen tube are determined to have the relationship of t1<t2. Consequently, when the expanding side of the multi-lumen tube gets thicker because fluid is supplied to the fluid-pressure actuator, the rupture of the multi-lumen tube can be prevented.

Figure 20:
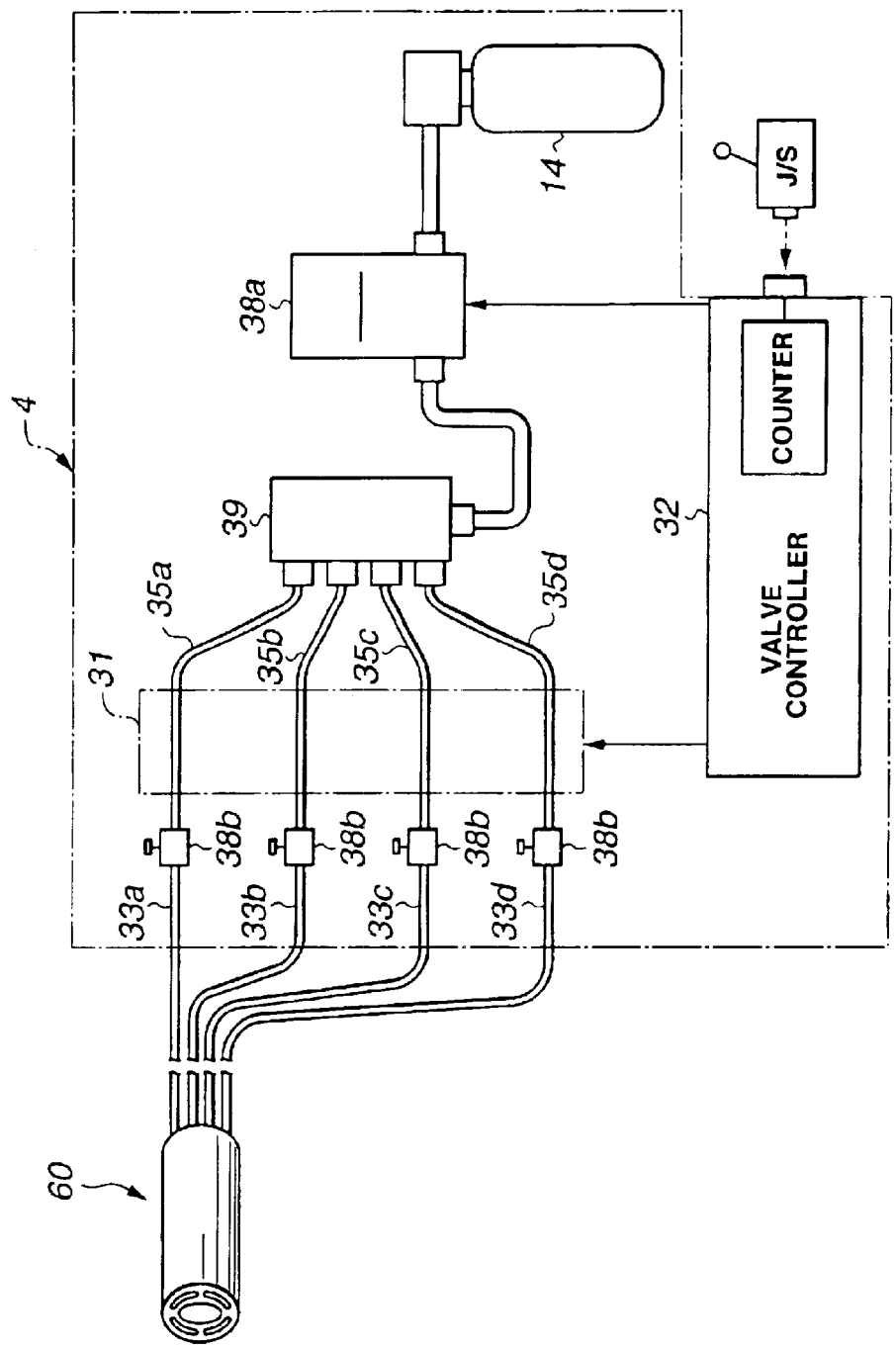
FIG. 20 is an explanatory diagram showing an endoscope that has regulation valves included in respective fluid supply tubes.

As shown in FIG. 20, an electropneumatic regulator 38a may be interposed between the gas cylinder 14 and tube coupling 39 incorporated in the drum 4. A regulation valve 38b may be interposed between each of the output terminals of the valve unit 31 and each of the fluid supply tubes 33a, 33b, 33c, and 33d. The electropneumatic regulator 38a regulates the pressure of fluid supplied from the gas cylinder 14. The regulation valves 38b are used to manually regulate the pressure of fluid fed to the fluid chambers.

The regulation valves 38b are included in the respective fluid supply tubes 33a, 33b, 33c, and 33d. Therefore, the amounts of fluid supplied from the valve unit 31 to the fluid chambers, which are associated with the respective bending directions, over the fluid supply tubes 33a, 33b, 33c, and 33d can be regulated in a well-balanced manner. Consequently, the amounts of fluid supplied to the fluid chambers formed in the fluid-pressure actuator 60 can be optimized using the regulation valves 38b. Eventually, the bending section can be bent in any direction in the same manner.

On the other hand, since the electropneumatic regulator 38a is included, when fluid is supplied to any of the fluid chambers of the fluid-pressure actuator 60 in order to bend the bending section 2b, the pressure of the fluid supplied to the fluid chamber can be decreased from a pressure P1 to a pressure P2 in desired steps. Thus, the pressure can be varied.

Figure 21:
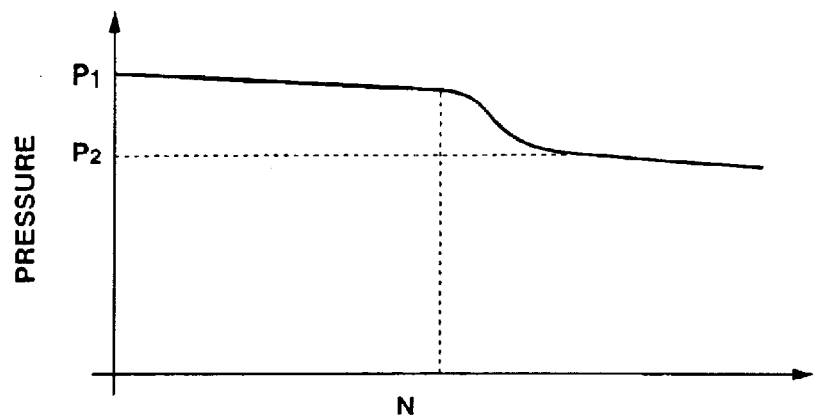
FIG. 21 is an explanatory diagram graphically showing the relationship between the pressure of fluid supplied to a fluid chamber and a frequency by which an electromagnetic valve is opened or closed.

Specifically, as indicated in FIG. 21, when the opening/closing motion of the electromagnetic valves has reached N times, the valve controller 32 transmits a directive signal to the electropneumatic regulator 38a so that the pressure of supplied fluid will be changed or decreased from the pressure P1 to the pressure P2.

Consequently, for example, the pressure of fluid supplied until the multi-lumen tube starts stretching axially and the pressure of fluid supplied thereafter may be differentiated from each other. In this case, the durability of the multi-lumen tube improves without a loss in a degree of bending.

According to the present embodiment, the thickness from the wall of the center through hole to the internal side of the wall of each penetrating hole formed in the multi-lumen tube is made different from the thickness from the external side of the wall of each penetrating hole to the periphery of the multi-lumen tube. This is intended to prevent the rupture of the multi-lumen tube 61 from occurring when fluid is supplied to the fluid-pressure actuator 60. As far as the position of a rupture is concerned, the rupture is predicted to occur more frequently near the base than in the center of the multi-lumen tube because of abrupt distortion.

Figure 22A:
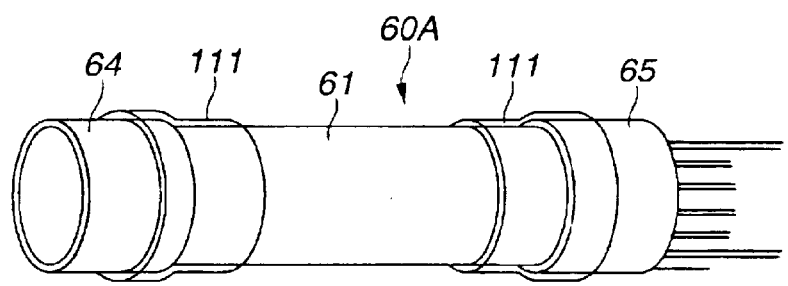
FIG. 22A shows a fluid-pressure actuator sheathed with base tubes.
Figure 22B:
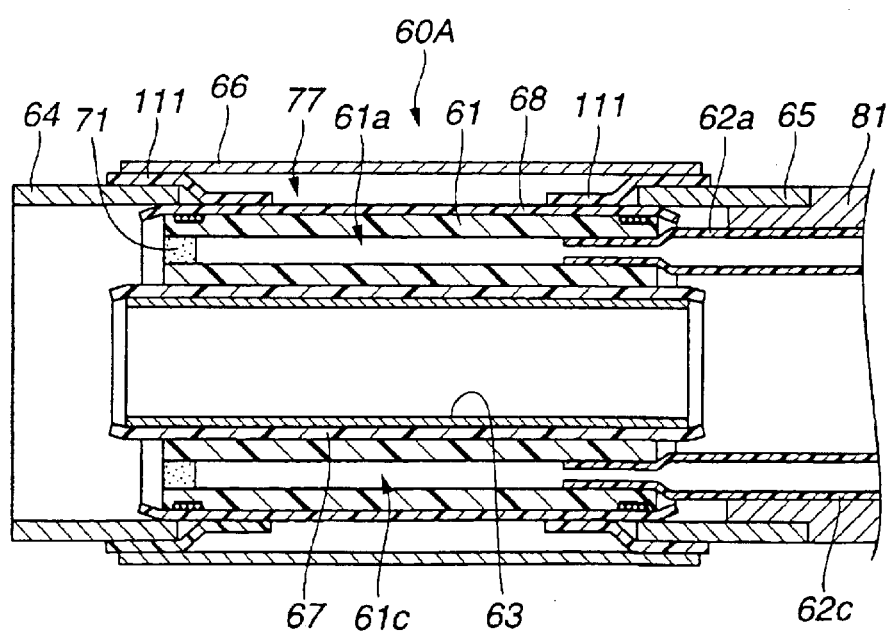
FIG. 22B is an explanatory sectional view showing a fluid-pressure actuator that has another structure.

Consequently, in a fluid-pressure actuator 60A shown in FIG. 22A and FIG. 22B, a base tube 111 having predetermined elasticity is adopted as a rupture preventing means in efforts to prevent the expansion of the multi-lumen tube 61 near the bases 64 and 65. Specifically, the distal part of the multi-lumen tube 61 on which the front base 64 and the outer tube 68 are put and the proximal part of the multi-lumen tube 61 on which the rear base 65 and the outer tube 68 are put are sheathed with the respective base tubes 111.

Figure 23A:
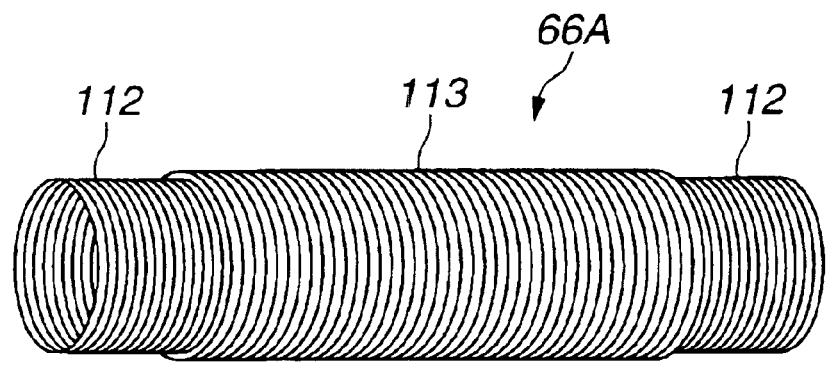
FIG. 23A shows a stepped external coil.
Figure 23B:
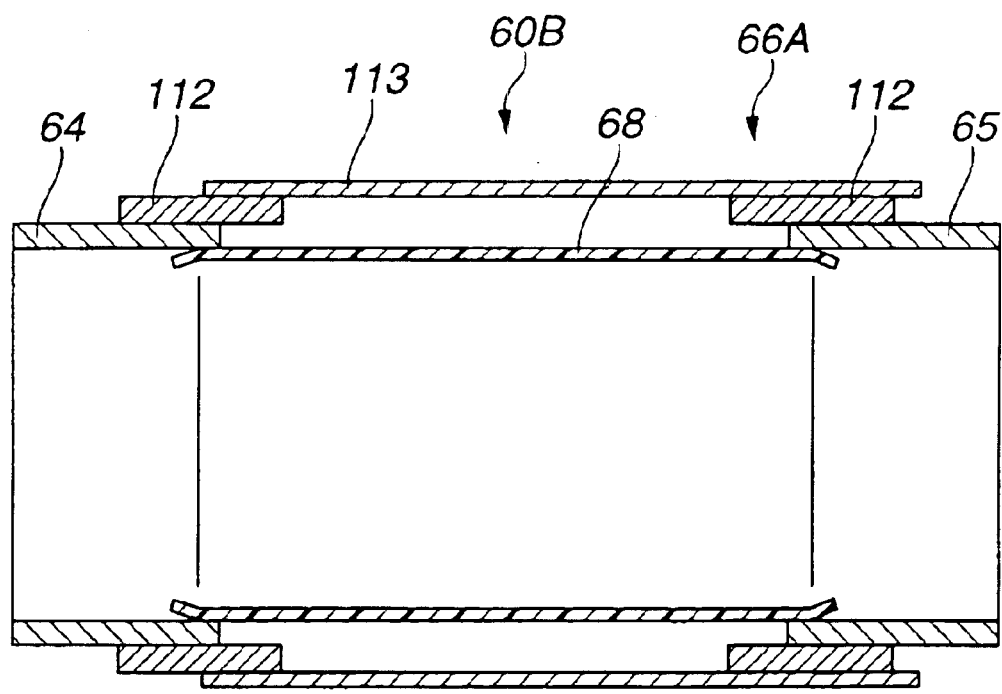
FIG. 23B shows a fluid-pressure actuator having another structure with the stepped external coil placed over it.

Moreover, as shown in FIG. 23A, a stepped external coil 66A having small-diameter coil portions 112 and a large-diameter coil portion 113 may be formed as a rupture preventing means. As shown in FIG. 23B, the stepped external coil 66A is placed so that the small-diameter portions 112 of the stepped external coil 66A will cover the bases 64 and 65 and the portions of the outer tube 68 adjoining the bases 64 and 65 alike. Thus, a fluid-pressure actuator 60B may be constructed.

Consequently, the expansion of the multi-lumen tube 61 near the bases 64 and 65 is suppressed, and occurrence of a rupture is largely reduced.

Figure 24A:
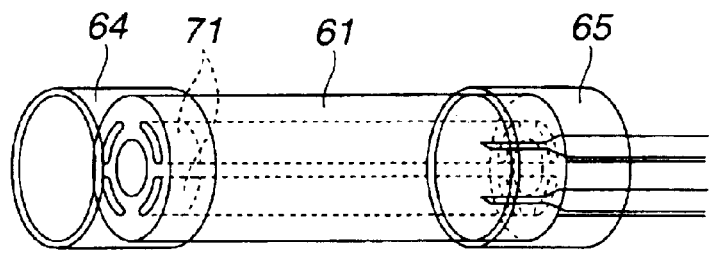
FIG. 24A shows a multi-lumen tube having bases attached thereto.

Furthermore, as shown in FIG. 24A, when the front base 64 and rear base 65 are attached to the ends of the multi-lumen tube 61, consideration is taken into the first adhesive portion 71 that is an occluded portion and the bobbin adhesive portions 74a and 74b. Specifically, the bases 64 and 65 are attached so that the end surfaces of he bases 64 and 65 will be located beyond the first adhesive portion 71 or the bobbin adhesive portions 74a and 74b. Thus, the first adhesive portion 71 and bobbin adhesive portions 74a and 74b can be protected from pressure applied by the fluid supplied to the air chambers.

Figure 24B:
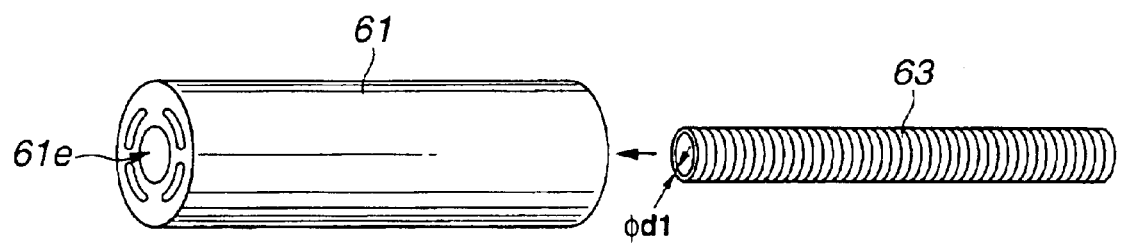
FIG. 24B is an explanatory diagram showing the multi-lumen tube and an internal coil.
Figure 24C:
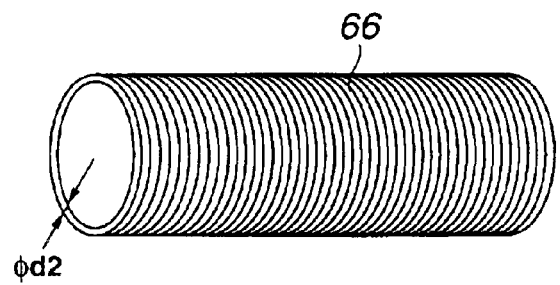
FIG. 24C is an explanatory diagram showing an external coil.

As shown in FIG. 24B and FIG. 24C, when the diameter (φd1) of a wire wound as the internal coil 63 is discussed in comparison with the diameter (φd2) of a wire wound as the external coil 66, a wire having a large diameter (φd1) is adopted for the internal coil 63 in consideration of the ease of insertion into the center through hole 61e. In contrast, a wire having a small diameter (φd2) is adopted for the external coil 66 in consideration of the ease of bending.

The outer diameter of the internal coil 63 sheathed with the inner tube (not shown) is a bit larger than the inner diameter of the center through hole 61e. The inner diameter of the external coil 66 is substantially identical to the outer diameter of the bases 64 and 65.

Figure 25:
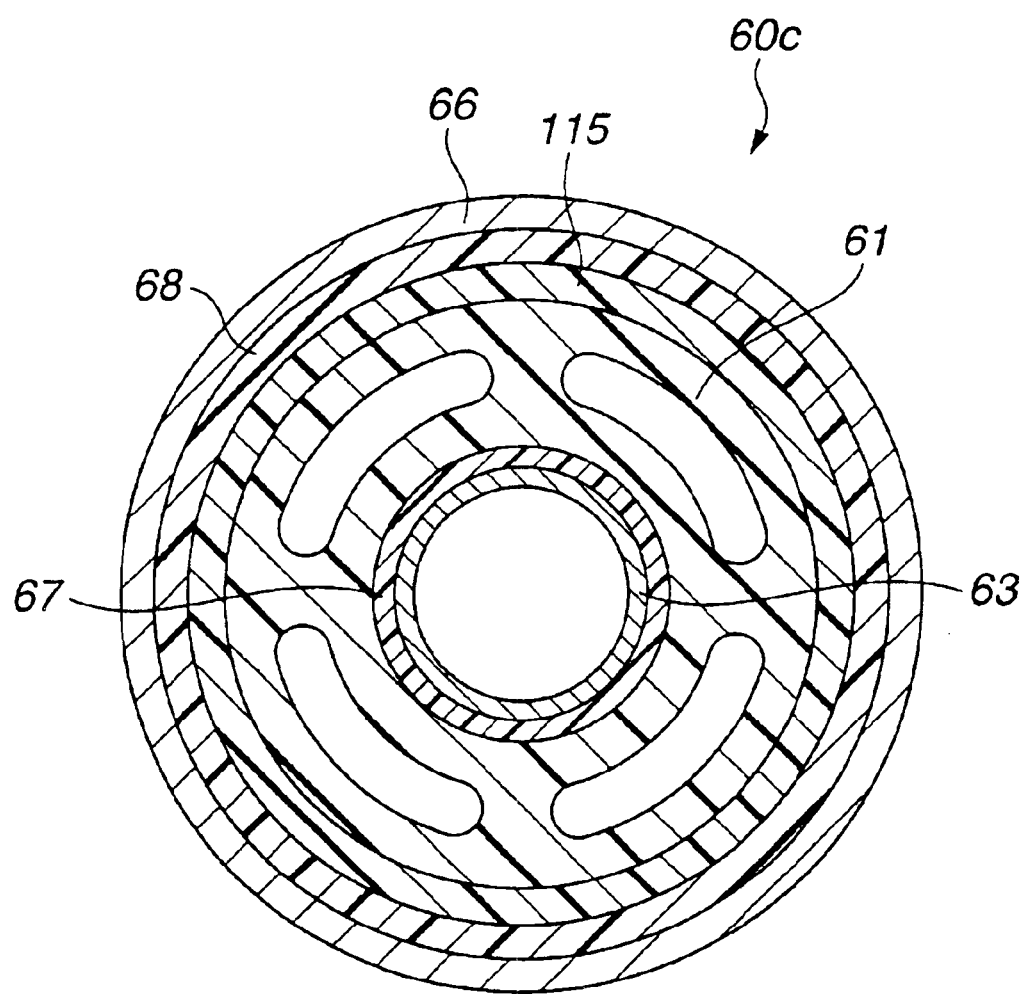
FIG. 25 is an explanatory diagram showing another structure of a fluid-pressure actuator.

As shown in FIG. 25, a protective member 115 having elasticity may be placed in the gap 77 created between the external coil 66 and the multi-lumen tube 61 sheathed with the outer tube 68. Thus, a fluid-pressure actuator 60C may be constructed.

In this case, the drawback that the multi-lumen tube 61 may be caught by adjoining ones of the turns of the external coil 66 or that the multi-lumen tube 61 may touch gas oil to expand can be avoided reliably.

Furthermore, in a conventional fluid-pressure actuator 120, the external coil 66 has, as shown in FIG. 26A, the ends thereof extended to the peripheries of the front and rear bases 64 and 65 in a natural manner. Therefore, an interspace is created between adjoining ones of the turns of the external coil 66. When the fluid-pressure actuator 120 is bent, the interspace gets larger. As the bending is repeated, the interspace between the adjoining ones of the turns of the external coil 66 becomes irregular. A rupture occurs frequently in a portion of the multi-lumen tube bared in a large interspace.

According to the present embodiment, the external coil 66 placed in a natural manner as shown in FIG. 26B is compressed by a dimension A indicated with arrows in FIG. 26C. The ends of the external coil 66 are put on the peripheries of the front and rear bases 64 and 65, whereby a fluid-pressure actuator 121 may be constructed. In this case, part of the external coil 66 becomes uneven as shown in FIG. 26D.

Figure 27A:
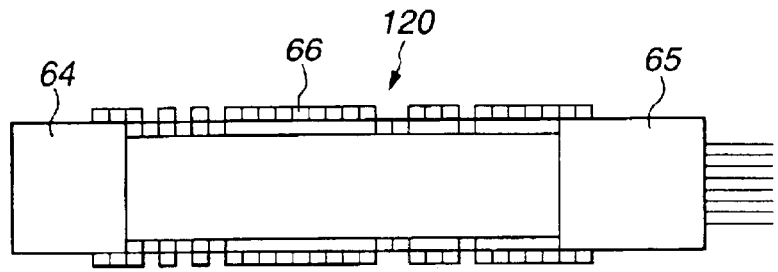
FIG. 27A shows a fluid-pressure actuator that has not yet been bent.

Assuming that fluid is supplied to the fluid-pressure actuator 120 having the ends of the compressed external coil 66 put on the front and rear bases 64 and 65 as shown in FIG. 27A, the fluid-pressure actuator 120 starts bending.

Figure 27B:
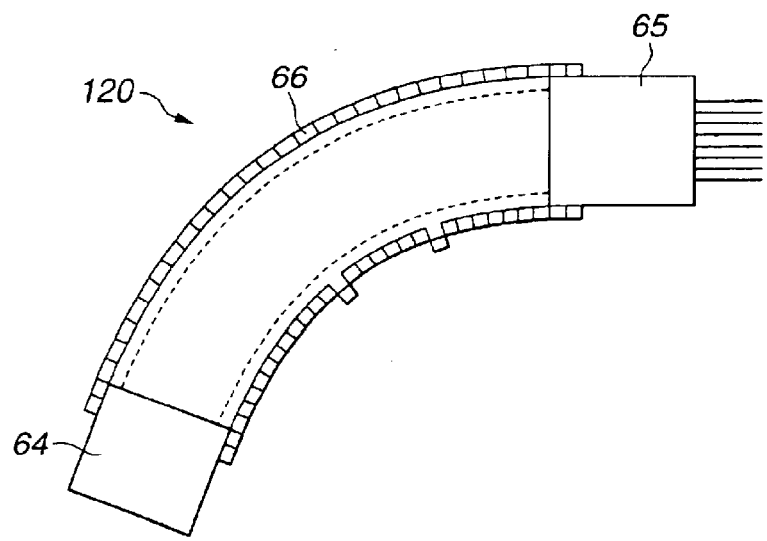
FIG. 27B shows the fluid-pressure actuator being bent.

First, as shown in FIG. 27B, the external side of the bent external coil 66 gradually stretches. Consequently, the uneven part of the external side of the bent external coil 66 is evened, and the unevenness in the external side is substantially nullified.

Figure 27C:
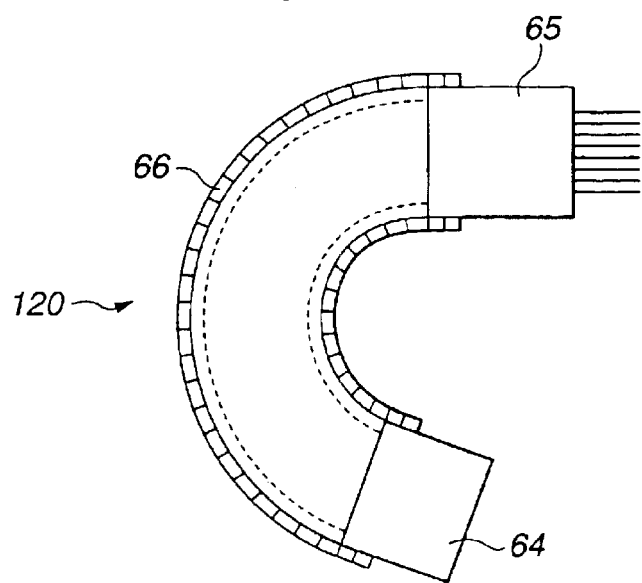
FIG. 27C shows the bent fluid-pressure actuator.

Thereafter, the fluid-pressure actuator 120 is further bent. This causes the internal side of the bent external coil 66 to stretch as shown in FIG. 27C. The uneven part of the internal side of the bent external coil 66 is evened, and the unevenness in the internal side is substantially nullified.

As mentioned above, the external coil included in the fluid-pressure actuator is compressed in advance and has the ends thereof put on the front and rear bases. Thus, the drawback that an interspace between adjoining ones of the turns of a coil gets large due to the repetitive bending of a fluid-pressure actuator can be avoided reliably.

Referring to FIG. 28 to FIG. 33E, another method of controlling the fluid-pressure actuator will be described below.

Figure 28:
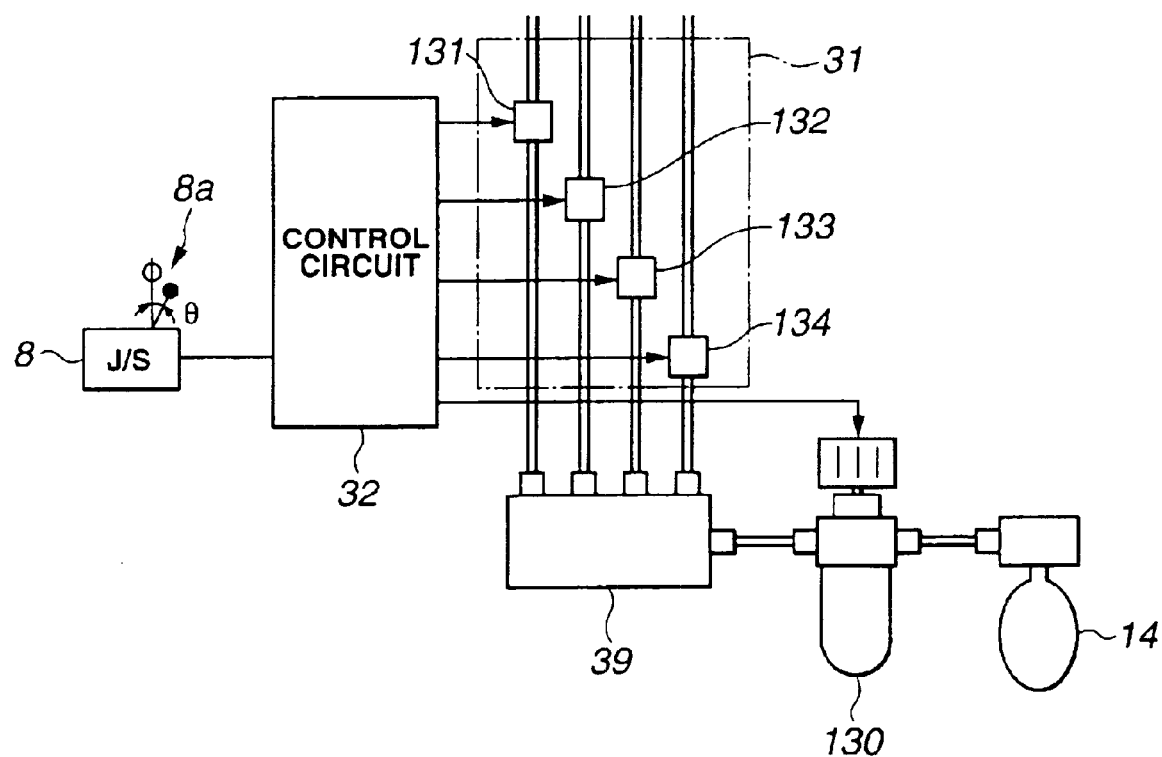
FIG. 28 is an explanatory diagram concerning the relationship between an electropneumatic regulator and valve control.

As shown in FIG. 28, according to the present embodiment, an electropneumatic regulator 130 is included as a fluid pressure source capable of varying the pressure of fluid by controlling a voltage. A directive signal sent from the valve controller 32 is transferred to the electropneumatic regulator 130.

When the joystick 8a of the remote controller 8 is tilted at an angle θ, a bending directive signal, and a timing signal indicating the angle at which the joystick is tilted and a time required until the fluid-pressure actuator is bent at an angle equivalent to the angle of tilting are transmitted from the remote controller 8 to the valve controller 32.

In response to the bending directive signal and timing signal sent from the remote controller 8, the valve controller 32 transmits a control signal to a predetermined electromagnetic valve unit 131, 132, 133, or 134 and the electropneumatic regulator 130 according to the tilting of the joystick 8a.

Consequently, a predetermined amount of nitrogen having a predetermined pressure is supplied from the electropneumatic regulator 130 to any fluid chamber of the fluid-pressure actuator 60 via the predetermined electromagnetic valve unit 131, 132, 133, or 134 so that the bending section 2b will be bent.

First, as indicated in FIG. 29A and FIG. 30A, a threshold is determined for the relationship between an angle at which the joystick 8a is tilted and a tilting speed.

Assume that the time required until the joystick 8a is tilted at an angle exceeds a time determined with the threshold as indicated in FIG. 29A. In this case, nitrogen whose pressure is set to P1 as indicated in FIG. 29B and which is supplied from the electropneumatic regulator 130 is, as indicated in FIG. 29C, fed to a fluid chamber via the electromagnetic valve unit 131, 132, 133, or 134 in a pulsating manner by a predetermined frequency at regular intervals during a time $\Delta t1$ according to a bending directive signal.

On the other hand, assume that the tilting speed at which the joystick 8a is tilted at an angle is, as indicated in FIG. 30A, equal to or smaller than the threshold. In this case, the pressure of nitrogen supplied from the electropneumatic regulator 130 is, as indicated in FIG. 30B, set to P2 lower than P1. The nitrogen is then, as indicated in FIG. 30C, fed to a fluid chamber via the electromagnetic valve unit 131, 132, 133, or 134 in a pulsating manner by the same frequency at regular intervals during the time $\Delta t1$.

When FIG. 29A to FIG. 29C are compared with FIG. 30A to FIG. 30C, the pressure of nitrogen supplied from the electropneumatic regulator 130 is different between FIG. 29B and FIG. 30B.

Namely, when the joystick 8a is tilted by taking a time exceeding a time determined with the threshold, the pressure of supplied nitrogen is set to a high pressure so that a bent shape will vary rapidly. Depending on whether a tilting speed at which the joystick 8a is tilted is lower or higher than the threshold, an amount of fluid to be supplied to a fluid chamber is varied. Thus, the bent or deformed state of the bending section can be varied.

As mentioned above, the tilting speed at which the joystick is tilted at a certain angle is regarded as a threshold. A tilting speed is compared with the threshold, and the pressure of nitrogen supplied from the electropneumatic regulator is varied in order to vary an amount of nitrogen fed to a fluid chamber via an electromagnetic valve unit. The bent or deformed state of the bending section is thus varied. Consequently, the deformed state of the bending section can be varied with a change in the handling of the joystick. This leads to improvement in the maneuverability of the bending section.

As indicated in FIG. 31A and FIG. 32A, two thresholds of first and second thresholds may be defined,-and the pressure of nitrogen may be varied according to the thresholds.

Assume that the joystick 8a is, as indicated in FIG. 31A, tilted at a small angle and the tilting speed exceeds the second threshold. In this case, nitrogen having a pressure P1 as indicated in FIG. 31B is, as indicated in FIG. 31C, fed from the electropneumatic regulator 130 via the associated electromagnetic valve unit 131, 132, 133, or 134 in a pulsating manner by a predetermined frequency at regular intervals during a time $\Delta t1$.

Moreover, when the tilting speed at which the joystick 8a is tilted is, as indicated in FIG. 31A, an intermediate value of the first and second thresholds, the pressure of nitrogen supplied from the electropneumatic regulator 130 is, as indicated in FIG. 31B, set to P2 that is indicated with a dot-dash line and that is lower than P1.

Furthermore, when the tilting speed is, as indicated in FIG. 31A, lower than the first threshold, the pressure of nitrogen supplied from the electropneumatic regulator 130 is, as indicated in FIG. 31B, set to a pressure P3 that is lower than the pressure P2 and that is indicated with an alternate long and two short dashes line in the drawing.

On the other hand, assume that, as indicated in FIG. 32A, the angle at which the joystick 8a is tilted is large and the tilting speed exceeds the second threshold. In this case, nitrogen having the pressure P1 as indicated in FIG. 32B is, as indicated in FIG. 32C, supplied from the electropneumatic regulator 130 via the associated electromagnetic valve unit 131, 132, 133, or 134 in a pulsating manner by a predetermined frequency at regular intervals during a time $\Delta t2$ longer than the time $\Delta t1$.

Consequently, the pressure value of nitrogen supplied from the electropneumatic regulator, one pulse duration, and an amount of nitrogen supplied to a fluid chamber are varied depending on whether the angle at which the joystick is large or small and whether the tilting speed determined with the angle is high or low. Thus, the bent or deformed state of the bending section responsive to the handling to the joystick can be varied.

Moreover, depending on whether a tilting speed is, as indicated in FIG. 33A, equal to or lower than the threshold, nitrogen of a predetermined pressure may be, as indicated with a dot-dash line in FIG. 33B and FIG. 33C, supplied from the electropneumatic regulator 130 via the valve unit 31. Otherwise, the valve unit 31 may be, as indicated with an alternate long and two short dashes line in FIG. 33D and FIG. 33E, left open, and the-pressure of nitrogen supplied from the electropneumatic regulator 130 may be varied. Thus, the bent or deformed state of the bending section 2b may be varied.

Specifically, when a speed at which the joystick. 8a is tilted is, as indicated in FIG. 33A, equal to or lower than the threshold, nitrogen of a pressure P1 indicated in FIG. 33C is, as indicated in FIG. 33B, supplied in a pulsating manner from the electropneumatic regulator 130 via the associated electromagnetic valve unit 131, 132, 133, or 134 by a predetermined frequency at regular intervals during a time $\Delta t1$.

Consequently, nitrogen is gradually supplied to a fluid chamber, and the bending section 2b is gradually bent or deformed.

On the other hand, when the speed at which the joystick 8a is tilted exceeds the threshold as indicated with an alternate long and two short dashes line in FIG. 33A, the valve unit 31 is left open as indicated in FIG. 33D. Thereafter, the pressure of nitrogen supplied from the electropneumatic regulator 130 is raised as indicated with an alternate long and two short dashes line in FIG. 33E. After nitrogen of a pressure that is higher by $\Delta p$ than the target pressure P1 is supplied, nitrogen whose pressure is returned to the target pressure P1 is supplied.

Consequently, nitrogen is supplied to a fluid chamber in the same manner as the supply is controlled by the electropneumatic regulator 130. The bending section 2b bends slowly first, and then bends at a gradually increasing angle.

Therefore, the bent or deformed state of the bending section can be varied depending on the tilting speed of the joystick 8a.

Referring to FIG. 34 to FIG. 37B, another method of controlling a fluid-pressure actuator will be described below.

Figure 34:
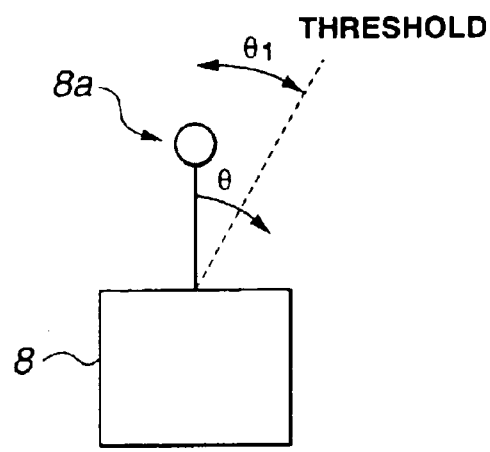
FIG. 34 is an explanatory diagram indicating the relationship between the angle at which the joystick is tilted and a threshold that is a predetermined angle.

According to the aforesaid control method, control is extended based on a threshold defined for the relationship between an angle at which the joystick 8a is tilted and a tilting speed. According to the present control method, a threshold is determined for the angle θ at which the joystick 8a is tilted as shown in FIG. 34. Namely, depending on whether the angle θ at which the joystick 8a is tilted exceeds a threshold θ1, the time during which nitrogen is supplied from the electropneumatic regulator 130 via an electromagnetic valve, an interval between adjoining supplies, and a frequency by which supply is repeated are controlled.

Figure 35:
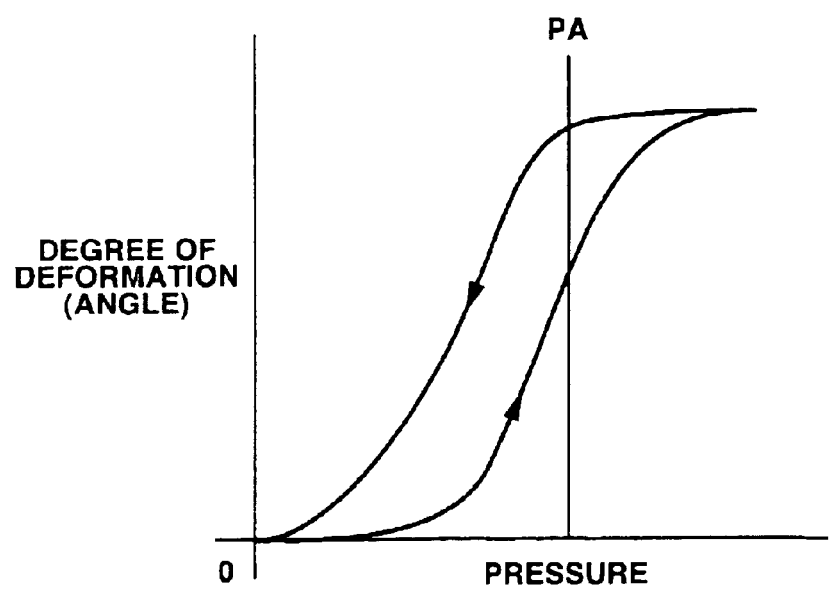
FIG. 35 graphically shows the relationship between the pressure of the bending section formed with the fluid-pressure actuator and a degree of bending deformation.

In the bending section 2b including the fluid-pressure actuator 60, the pressure of nitrogen and an angle of bending that is a change in the shape of the bending section have a relationship indicated in FIG. 35.

As seen from FIG. 35, a degree of bending deformation of the bending section 2b including the fluid-pressure actuator 60 is very small relative to a change in the pressure of fluid immediately after the start of raising the pressure. When the pressure exceeds a certain value, the degree of bending deformation varies largely relative to a slight change in the pressure. Thereafter, the degree of bending deformation varies moderately relative to the change in the pressure.

In the graph, a point PA is a turning point. When a pressure is lower by a predetermined value from a pressure A, an abrupt deformation occurs despite a small change in the pressure. An initial amount of supplied fluid is therefore set to a small amount. When the pressure gets larger than the pressure PA, the amount of supplied fluid increases. Consequently, the bending section 2b can be bent evenly responsively to the tilting of the joystick 8a.

Therefore, when the joystick 8a is tilted, control is extended differently as indicated in FIG. 36A and FIG. 36B or FIG. 37A and FIG. 37B according to whether the angle θ at which the joystick is tilted is smaller or larger than the angle θ1.

Figure 36A:
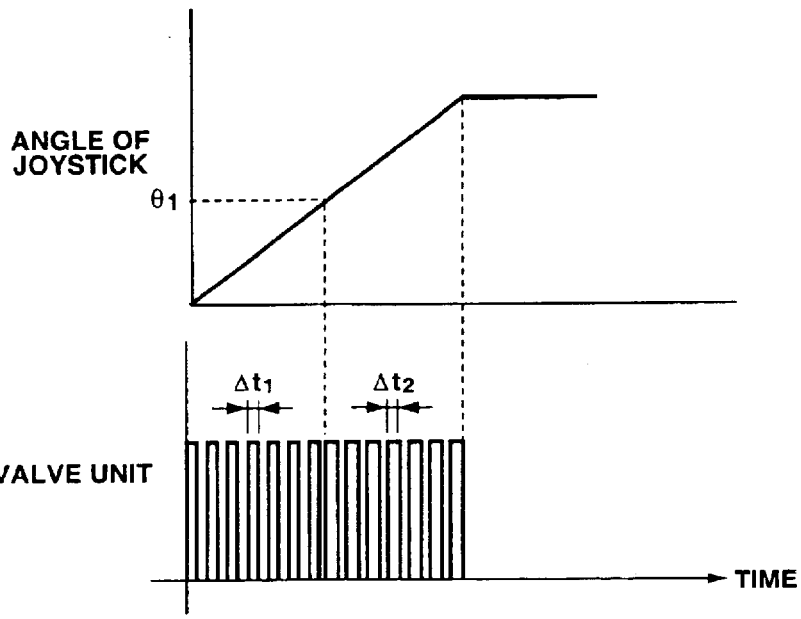
FIG. 36A indicates the angle at which the joystick is tilted.
Figure 36B:
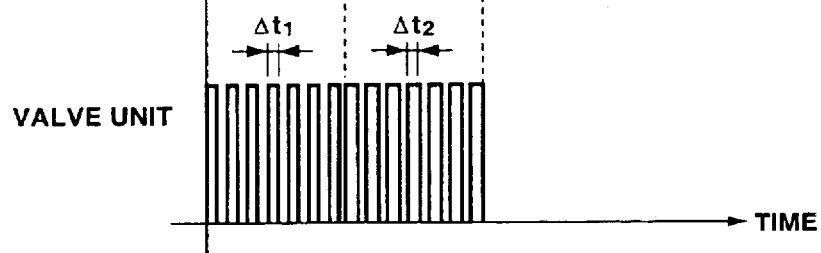
FIG. 36B indicates an example of the relationship between the angle at which the joystick is tilted and the supply of fluid from the valve unit.

Specifically, when the angle θ at which the joystick 8a is tilted is, as indicated in FIG. 36A, smaller than the angle θ1, nitrogen is, as indicated in FIG. 36B, supplied to a fluid chamber via the valve unit 31 using a predetermined set pressure by a predetermined frequency at regular intervals during a time Δt1.

On the other hand, when the angle θ at which the joystick 8a is tilted is, as indicated in FIG. 36A, larger than the angle θ1, nitrogen is, as indicated in FIG. 36B, supplied to a fluid chamber via the valve unit 31 using a predetermined set pressure by a predetermined frequency at regular intervals during a time Δt2 that is longer than the time Δt1. At this time, the interval between adjoining supplies is substantially identical to the interval between adjoining ones of supplies performed during the time Δt1.

Figure 37A:
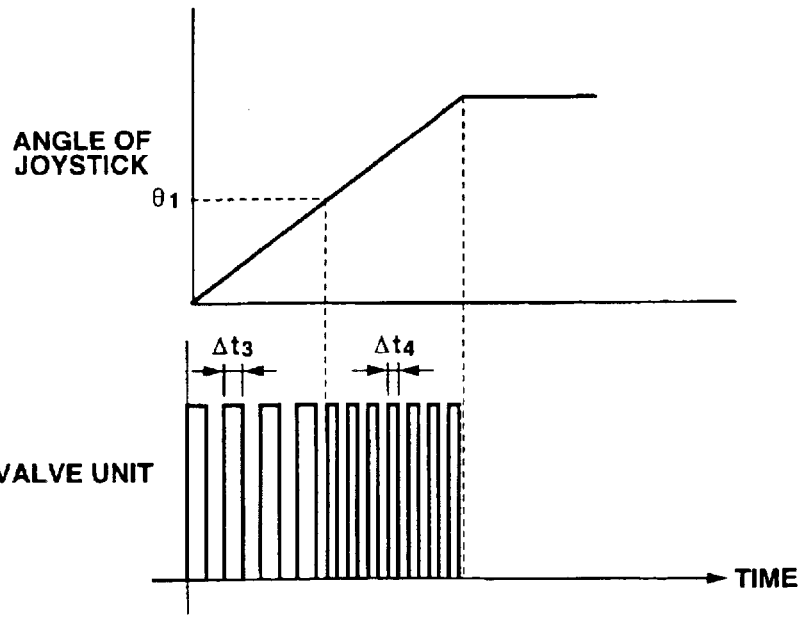
FIG. 37A indicates the angle at which the joystick is tilted.
Figure 37B:
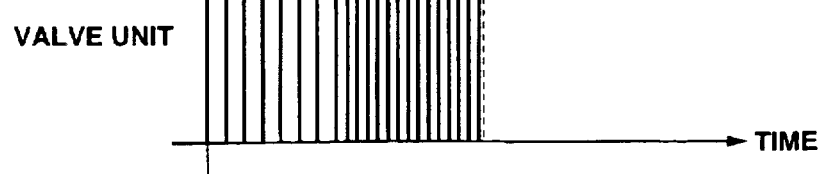
FIG. 37B indicates another example of the relationship between the angle at which the joystick is tilted and the supply of fluid from the valve unit.

In contrast, when the angle θ at which the joystick 8a is tilted is, as indicated in FIG. 37A, smaller than the angle θ1, nitrogen is, as indicated in FIG. 37B, supplied to a fluid chamber via the valve unit 31 using a predetermined set pressure by a predetermined frequency at regular intervals during a time Δt3.

On the other hand, when the angle θ at which the joystick 8a is tilted is, as indicated in FIG. 37A, larger than the angle θ1, nitrogen is, as indicated in FIG. 37B, supplied to a fluid chamber via the valve unit 31 using a predetermined set pressure by a predetermined frequency at regular intervals during a time Δt4 that is substantially identical to or slightly shorter than the time Δt3. At this time, the interval between adjoining supplies is shorter than the interval between adjoining ones of supplies performed during the time Δt3.

In either case, when the angle θ at which the joystick 8a is tilted is equal to or smaller than the angle θ1, nitrogen is gradually supplied to a fluid chamber in order to prevent a degree of bending deformation of the bending section from changing abruptly. Moreover, when the angle θ at which the joystick 8a is tilted is set to a large angle exceeding the angle θ1, a large amount of nitrogen is rapidly supplied to a fluid chamber so that the bending section can be bent largely smoothly.

Consequently, the drawback in a characteristic concerning a pressure and a degree of bending deformation of the bending section which is indicated in FIG. 35 is resolved.

Referring to FIG. 38 to FIG. 41, a still another control method for a fluid-pressure actuator will be described below.

Figure 38:
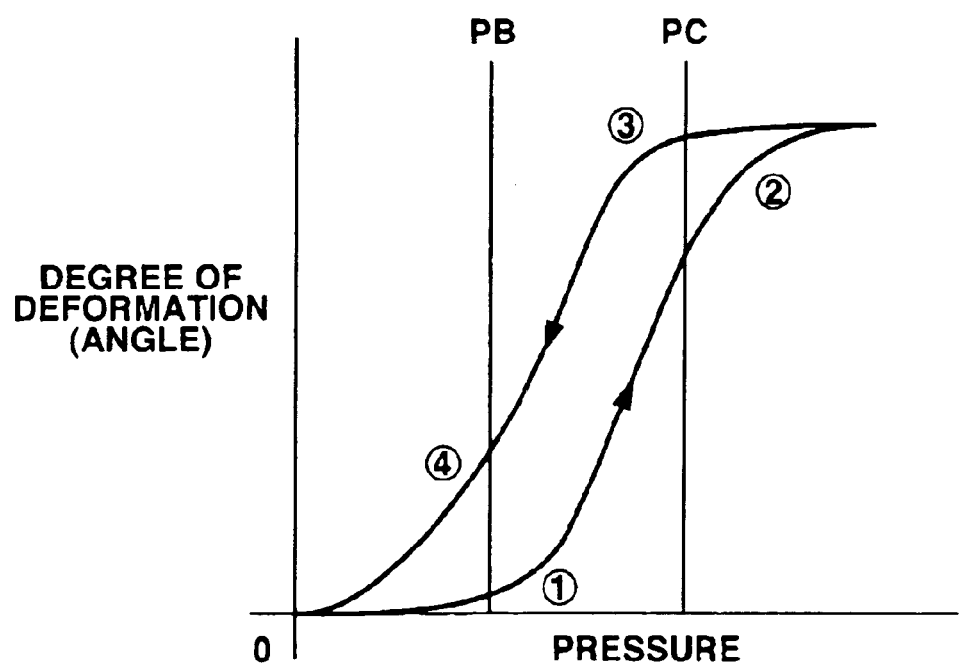
FIG. 38 is an explanatory diagram indicating turning points of pressures.

According to the present control method, as indicated in FIG. 38, two turning points are set at points of pressures PB and PC. Namely, when a pressure is smaller than PB, even if the pressure varies relatively largely, the degree of bending deformation of the bending section is limited. In contrast, when a pressure ranges from PB to PC, even if the pressure varies a bit, the degree of bending deformation of the bending section is large. When a pressure is equal to or larger than PC, similarly to when a pressure is smaller than PB, even if the pressure varies relatively largely, the degree of bending deformation of the bending section is limited.

When a pressure is equal to or smaller than PB, a degree of deformation is limited. At this time, even when a user handles the joystick 8a, the user will not perceive the bending deformation of the bending section 2b. It is desired that a user will perceive the bending deformation of the bending section 2b responsively to his/her handling of the joystick 8a. The pressure PB at a turning point is found near a point at which an abrupt rise starts and a point at which a drop becomes moderate. The turning point PC is found near a point at which a rise decreases and a point at which a drop starts increasing abruptly.

Figure 39A:
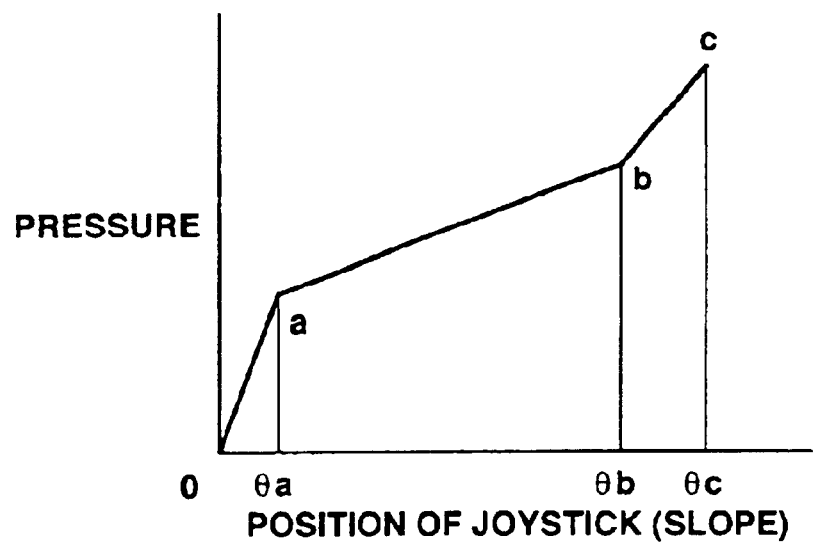
FIG. 39A is an explanatory diagram indicating the relationship between the angle at which the joystick is tilted and the supplied pressure value.

According to the present embodiment, assuming that a pressure ranges from PB to PC as indicated in FIG. 38, when the joystick 8a is tilted as indicated in FIG. 39A, the pressure rises little by little. This is intended to prevent the bent state of the bending section from changing abruptly largely despite a limited change in the pressure. Consequently, when the joystick 8a is moved little by little, the change in the shape of the bending section 2b varies responsively to the handling of the joystick.

Figure 39B:
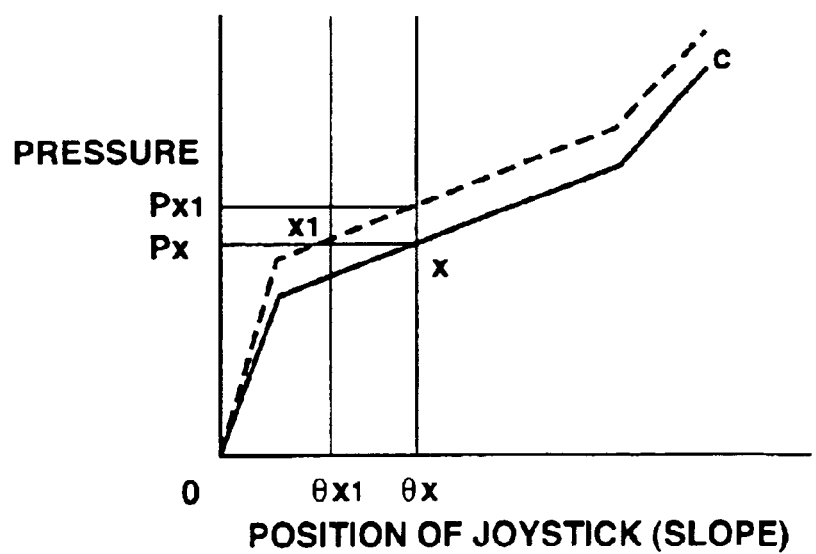
FIG. 39B is an explanatory diagram indicating the relationship between the angle at which the joystick is tilted and an actually supplied pressure value.

In contrast, assuming that a pressure is, as indicated in FIG. 38, equal to or smaller than PB or equal to or larger than PC, the bending deformation of the bending section 2b is, as indicated in FIG. 39B, limited relative to a change in the pressure. Therefore, a pressure is determined so that it will change largely responsively to the slight tilting of the joystick 8a. Consequently, even when an angle at which the joystick 8a is handled is small, if the pressure is changed relatively largely, the bending section is deformed responsively to the handling of the joystick 8a.

When a pressure is equal to or smaller than PB, compared with when a pressure is equal to or larger than PC, the pressure largely rises responsively to the slight tilting of the joystick 8a.

As mentioned above, when a rise in a pressure is varied depending on an angle at which the joystick is handled, the bending section can be bent smoothly irrespective of the angle at which the joystick is tilted.

Incidentally, the points PB and PC can be changed appropriately.

Moreover, when an endoscope is of a type that nitrogen is supplied to a fluid chamber according to the tilting of a joystick in order to bend a bending section, a predetermined time is needed until the fluid chamber is filled with the nitrogen. Therefore, there is a time lag from the instant the joystick is handled to the instant a fluid chamber is filled with nitrogen. A drawback that the tilting of the joystick does not coincide with bending operation.

In order to resolve the above drawback, when a change in a pressure responsive to the handling of the joystick should be defined as indicated with a solid line in FIG. 39B, a larger change in a pressure indicated with a dashed line is adopted.

For example, when the joystick is tilted at an angle θx1, adoption of a pressure Px indicated with the dashed line is directed. In principle, the pressure Px is associated with the inclination θx of the joystick. In other words, the setting of a pressure is determined relative to an increased value of the inclination of the joystick. Consequently, the bending section can be bent or the shape of the bending section can be changed substantially responsively to the user's handling of the joystick. A feeling that the bending of the bending section lags behind the handling of the joystick is resolved. Therefore, a feeling that the bending of the bending section is inconsistent with the tilting of the joystick is nullified, and the bending section can be operated smoothly.

Figure 40:
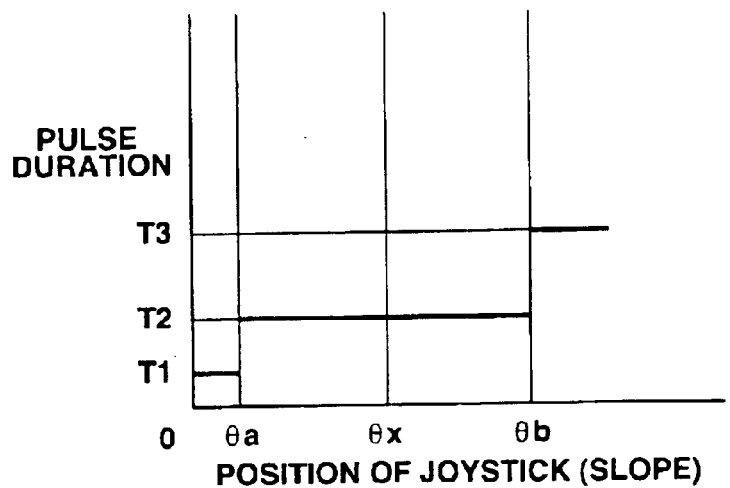
FIG. 40 is an explanatory diagram indicating the relationship between the angle at which the joystick is tilted and the time during which the valves are left open.

Furthermore, instead of changing a pressure according to the angle at which the joystick 8a is tilted, the time during which nitrogen is supplied may be, as indicated in FIG. 40, varied depending on the angle at which the joystick 8a is tilted.

Figure 41:
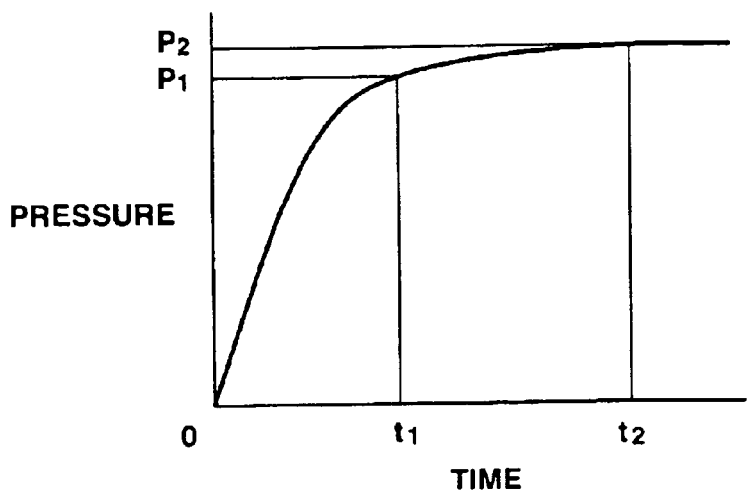
FIG. 41 indicates an example of a control method that takes account of a time lag of fluid supply.

Moreover, assume that a pressure should be set to, for example, a pressure P2 as indicated in FIG. 41 in order to resolve the feeling that the bending of the bending section lags behind the handling of the joystick. In this case, a pressure P1 that can be attained for a relatively short period of time and that is lower than the pressure P2 is adopted as a set value instead of the pressure P2 according to a curve indicating a change in a pressure. In this case, the aforesaid time lag can be overcome.

Having described the preferred embodiments of the invention referring to the accompanying drawings, it should be understood that the present invention is not limited to those precise embodiments and various changes and modifications thereof could be made by one skilled in the art without departing from the spirit or scope of the invention as defined in the appended claims.

What is claimed is:

1. An endoscope whose bending section is moved with supply or discharge of fluid, comprising:
    a fluid-pressure actuator that is included in the bending section of an insertion unit and that has a plurality of fluid chambers associated with a plurality of bending directions; and
    fluid supply tubes over which fluid is supplied to the fluid chambers included in the fluid-pressure actuator or over which fluid supplied to the fluid chambers is discharged,
    wherein the fluid-pressure actuator comprises:
    a soft multi-lumen tube having a center through hole and a plurality of penetrating holes that surrounds the center through hole and that realizes the fluid chambers;
    an internal tubular member inserted in the center through hole; and
    an external tubular member put on the periphery of the multi-lumen tube with a gap, which allows each fluid chamber to axially stretch and radially slightly expand during supply of fluid to the fluid chamber and thus eases bending, created between them.

2. An endoscope according to claim 1, wherein the internal tubular member and the external tubular member are coil members.

3. An endoscope according to claim 1, wherein: the fluid-pressure actuator included in the bending section further comprises bases that are attached to the distal and proximal ends of the multi-lumen tube and that serve as gap creation members; and the external surfaces of the bases attached to the multi-lumen tube are covered with the external tubular member, whereby a gap is created between the periphery of the multi-lumen tube and the internal surface of the external tubular member.

4. An endoscope according to claim 1, wherein the bending section of the insertion unit further comprises a bending cover that is put on the periphery of the fluid-pressure actuator with a gap created between them.

5. An endoscope according to claim 4, wherein the length of the bending cover is made larger than the length of the fluid-pressure actuator for the purpose of creating the gap.

6. An endoscope according to claim 4, wherein the inner diameter of the bending cover is made larger than the outer diameter of the fluid-pressure actuator for the purpose of creating the gap.

7. An endoscope according to claim 1, wherein a distance (t1) from the wall of the center through hole to the internal side of the wall of each of the penetrating holes formed in the multi-lumen tube and a distance (t2) from the external side of the wall of each of the penetrating holes to the periphery of the multi-lumen tube have a relationship of t1<t2.

8. An endoscope according to claim 3, wherein the fluid-pressure actuator included in the bending section further comprises: thin tubes interposed between the multi-lumen tube and the internal tubular member or between the multi-lumen tube and the external tubular member; and an exhaust discharging means for discharging gas, which stays between each of the thin tubes and the multi-lumen tube, to outside.

9. An endoscope according to claim 8, wherein the exhaust discharging means is a tubular body, and the tubular body is interposed between each of the thin tubes and the multi-lumen tube.

10. An endoscope according to claim 8, wherein the exhaust discharging means is realized with exhaust channels formed in the bases attached to the respective ends of the multi-lumen tube.

11. An endoscope according to claim 8, wherein the exhaust discharging means is realized with slits formed in the thin tubes.

12. An endoscope according to claim 8, wherein the exhaust discharging means is realized with exhaust holes formed in the thin tubes.

13. An endoscope according to claim 8, wherein the exhaust discharging means is realized with an uneven part of the thin tubes.

14. An endoscope according to claim 8, wherein the exhaust discharging means is realized with the thin tubes formed with porous members.

15. An endoscope according to claim 8, wherein the fluid-pressure actuator included in the bending section further comprises a rupture preventing means for preventing a rupture that is caused by a distortion which occurs abruptly and that is likely to occur near the bases attached to the multi-lumen tube.

16. An endoscope according to claim 15, wherein the rupture preventing means is realized with base tubes that are put on the ends of the multi-lumen tube which are covered with the respective bases and thin tubes, and that have elasticity.

17. An endoscope according to claim 15, wherein the rupture preventing means is realized with a stepped external coil that includes small-diameter coils put on the ends of the multi-lumen tube which are covered with the respective bases and thin tubes, and a large-diameter coil whose diameter is larger than the diameter of the small-diameter ends.

18. An endoscope according to claim 1, further comprising:
- a drum about which the insertion unit is wound and in which a fluid pressure source that supplies fluid to the fluid-pressure actuator and a fluid supply level control unit that controls fluid supplied from the fluid pressure source are incorporated; and
- a remote controller that transmits a directive signal to a valve controller included in the fluid supply level control unit so as to direct supply of fluid to each fluid chamber included in the fluid-pressure actuator or discharge of fluid from the fluid chamber, and that includes a joystick used to direct the bending section to bend.

19. An endoscope according to claim 18, wherein the fluid supply level control unit defines a predetermined threshold in relation to the tilting of the joystick, and controls the pressure of fluid to be supplied from the fluid pressure source to each fluid chamber, a time during which fluid is supplied, an interval between adjoining supplies, and a frequency by which supply is repeated according to whether the predetermined threshold is exceeded.

20. An endoscope according to claim 19, wherein the threshold is defined for the relationship between an angle at which the joystick is tilted and a tilting speed.

21. An endoscope according to claim 19, wherein the threshold is defined for an angle at which the joystick is tilted.

22. An endoscope according to claim 18, wherein the drum accommodates: a gas cylinder that maintains a high pressure and supplies fluid to the fluid-pressure actuator; a regulator that controls the pressure of the gas cylinder; a valve unit that has a plurality of electromagnetic valve units associated with the fluid chambers of the fluid-pressure actuator; and a fluid pressure source that includes tubes which communicate with the respective fluid chambers of the fluid-pressure actuator and over which fluid is supplied.

23. An endoscope according to claim 22, wherein the drum further accommodates: an electropneumatic regulator that is interposed between the gas cylinder and the valve unit and that regulates the pressure of fluid to be supplied from the gas cylinder; and regulation valves that are interposed between the respective output terminals of the valve unit and the respective tubes and that are used to manually regulate the pressure of fluid to be supplied to each fluid chamber.

* * * * *